«12» United States Patent
Scheinberg et al.

(10) Patent No.: US 6,683,162 B2
(45) Date of Patent: Jan. 27, 2004

(54) TARGETED ALPHA PARTICLE THERAPY USING ACTINIUM-255 CONJUGATES

(75) Inventors: David Scheinberg, New York, NY (US); Dangshe Ma, Rockville, MD (US); Michael McDevitt, Bronx, NY (US); Paul Borchardt, New York, NY (US)

(73) Assignee: Sloan Kettering Institute of Cancer Research, New York, NY (US)

( * ) Notice: Subject to any disclaimer, the term of this patent is extended or adjusted under 35 U.S.C. 154(b) by 0 days.

(21) Appl. No.: 09/952,756

(22) Filed: Sep. 14, 2001

(65) Prior Publication Data

US 2002/0058007 A1 May 16, 2002

Related U.S. Application Data

(60) Provisional application No. 60/232,909, filed on Sep. 15, 2000, now abandoned.

(51) Int. Cl.[7] .................................................. C07F 5/00
(52) U.S. Cl. ........................ 534/11; 424/1.11; 424/1.69; 424/1.49; 534/11; 514/2; 514/183; 514/471
(58) Field of Search ......................... 534/7, 10–16; 424/1.11, 1.65, 1.49, 1.69, 9.1, 9.3, 9.4, 9.5, 9.6, 9.7, 9.8; 514/2, 9, 156, 183, 471

(56) References Cited

U.S. PATENT DOCUMENTS

2002/0006379 A1 * 1/2002 Hansen et al. ............. 424/1.49

* cited by examiner

Primary Examiner—Dameron L. Jones
(74) Attorney, Agent, or Firm—Benjamin Aaron Adler

(57) ABSTRACT

The present invention provides functionalized chelants and a method of treating cancerous cells with alpha particles comprising the step of administering a pharmacologically effective dose of an $^{225}$Ac conjugate comprising a functionalized chelant

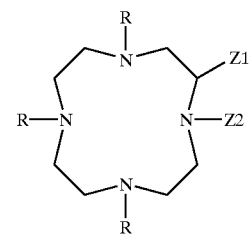

R is independently $CHQCO_2X$; Q is independently hydrogen; C1–C4 alkyl or (C1–C2 alkyl) phenyl; X is independently hydrogen; benzyl or C1–C4 alkyl; Z1 is $(CH_2)_nY$ where n is 1–10 and Y is an electrophilic or nucleophilic moiety and Z2 is R; or, alternatively, Z1 is hydrogen and Z2 is a peptide linker composed of 1–10 amino acids; said Y or said peptide linker covalently attached to an antibody or fragment thereof, or other biologic molecule; or a pharmaceutically acceptable salt thereof, complexed with $^{225}$Ac. These biologic molecule binds to cancerous cells and $^{225}$Ac or its daughters emit alpha particles into said cancerous cells effecting treatment.

20 Claims, 13 Drawing Sheets

TARGETED ALPHA PARTICLE THERAPY USING ACTINIUM-255 CONJUGATES

CROSS-REFERENCE TO RELATED APPLICATION

This non-provisional patent application claims benefit of provisional patent application U.S. Ser. No. 60/232,909, filed Sep. 15, 2000, now abandoned.

FEDERAL FUNDING LEGEND

This invention was produced in part using funds obtained through grants RO1 CA55349 and PO1 33049 from the National Institutes of Health. Consequently, the federal government has certain rights in this invention.

BACKGROUND OF THE INVENTION

1. Field of the Invention

The present invention relates generally to the fields of radionuclide chemistry and radioimmunotherapy. More specifically, the present invention relates to bifunctional chelates of actinium-225 and their uses in targeted immunotherapy.

2. Description of the Related Art

Alpha particles are high energy, high linear energy transfer (LET) helium nuclei capable of enormous, yet selective cytotoxicity (1). A single atom emitting an alpha particle can kill a target cell (2). Monoclonal antibodies conjugated to alpha-particle emitting radionuclides ($^{234}$Bi and $^{211}$At) are being used as radioimmunotherapeutic agents (RIT) (3,4). In a preclinical setting [213Bi]HuM195 (2) and [213Bi]J591 (5,6) have been implemented for the treatment of leukemia and prostate cancer, respectively. Additionally, a phase I human clinical trial using cumulative doses of up to 3.7 GBq (100 mCi) of administered [213Bi]HuM195 has shown no significant normal tissue toxicity, yet major tumorocidal activity for leukemia cells (3) thus demonstrating the safety, utility, and potency of targeted alpha-particle therapy in humans. $^{211}$At labeled anti-tenascin antibodies have been used clinically to treat human neural neoplasma (4) in a phase I trial.

For clinical use of $^{213}$Bi, a therapeutic dose-level $^{225}$Ac/$^{213}$Bi generator device, approximately 1×6 cm in size, capable of producing alpha particle emitting atoms for attachment to ligands, suitable for human injection (7,8) has been developed. Despite this improvement, the major obstacle to the widespread use of these drugs is the short $^{213}$Bi half-life (46 min) which effectively limits its delivery to only the most accessible cancers. Furthermore, this short half-life requires the generator device itself to be available near the patient.

By delivering the generator to the target cell, atoms are produced that yield potent alpha-emissions at or in the cancer cell. For this process to be successful pharmacologically, the device needed to possess molecular dimensions. At its ultimate reduction the device therefore consists of a single generator atom attached to the delivery vehicle. Generator technology optimally requires the use of a long-lived parent isotope that produces short-lived, alpha emitters. Moreover, methods to stably attach the generator to a targeting vehicle and an understanding of the fate of the daughter alpha-emitting atoms are needed.

Actinium-225 has a 10.0 day half-life and decays via alpha emission through 3 atoms, each of which also emits an alpha particle (9, 10). Once inside the cell, the geometry of the decay trajectory of the alpha particle favors highly efficient cell killing: each decay must pass through the cell, whereas statistically only 30% of the alpha decays will pass through the cells if the generator is surface bound (2). Relative to $^{213}$Bi, the longer half-life of $^{225}$Ac allows more efficient delivery of atoms to the cell and then into the cell. Selection of tumor antigen systems that internalize the generator help to contain the daughters and therefore lead to enhanced potency; however, internalization is not required for activity.

Actinium-225 is thus attractive for clinical generator applications. The long half-life and the four net alpha-particles emitted by the $^{225}$Ac, provide additional time to target, to penetrate, and to treat solid tumors in vivo. Such an actinium-225 generator possesses far greater potency (313-fold greater $^{225}$Ac half-life than $^{213}$Bi) than any other cytotoxic agents. More efficient cytotoxicity following intracellular delivery of the generator is effected, i.e., a single molecule can kill a targeted cell Thus, little radioactivity (possible sub-GBq (mCi) levels) would be required for therapeutic human use, allowing for economical outpatient use and safety. The manufacture and quality control of a radiolabeled generator construct can be effected at a central radiopharmacy site and the shipped throughout the world. Stable attachment of the $^{225}$Ac to the targeting ligand, e.g., monoclonal antibody, followed by delivery and internalization by the target cell allows potential retention of the device and the entire atomic cascade within the target, thereby increasing the efficacy and reducing bystander effects. The short range of the emitted alpha particles limit the non-specific radiation dose to surrounding cells and provide a high therapeutic ratio.

Previously, $^{225}$Ac-based drug constructs employing chelates have been deemed too unstable with the daughters presenting an untenable pharmacological problem (21–25). The development of synthetic methods to yield stable nanoscale generator constructs of [225Ac]IgG in useful quantities and the demonstration of safe, efficacious deployment against models of both disseminated cancer and solid carcinomas using very small doses of isotope, suggests a pathway to widespread clinical use of such targeted drugs. Thus, a means of safely and efficaciously using $^{225}$Ac as a stable and tumor-selective molecular sized generator in both disseminated cancers or established solid carcinomas is desirable. The prior art is deficient in the lack of effective actinium-225 chelates and complexes beneficial for targeted radioimmunotherapy. The present invention fulfills this long-standing need and desire in the art.

SUMMARY OF THE INVENTION

In one embodiment of the present invention there is provided an $^{225}$Ac complex comprising a functionalized chelant compound having the structure

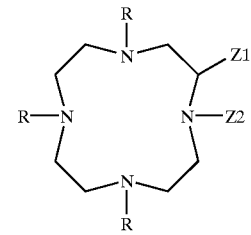

where R is independently CHQCO2X; Q is independently hydrogen; $C_{1-4}$-alkyl or ($C_{1-2}$-alkyl) phenyl; X is independently hydrogen; benzyl or alkyl; Z1 is $(CH_2)_n Y$ wherein n is 1–10 and Y is an electrophilic or nucleophilic moiety and Z2 is R; or, in the alternative, Z1 is hydrogen and Z2 is a peptide linker composed of 1–10 amino acids; said Y or said peptide linker covalently attached to an antibody or fragment thereof, or other biologic molecule with the proviso that when R and Z2 are $CH_2CO_2H$, Z1 is not $CH_{(1-6)}Y$ wherein Y comprises a para-substituted phenyl group, said phenyl substituent having a free end group comprising —$NO_2$, —$NH_2$, —NCS, —COOH, —$OCH_2COOH$, —$OCH_2COOH$, $NHCOCH_2Br$ or $NHCOCH_2I$; or a pharmaceutically acceptable salt thereof; complexed with $^{225}Ac$.

In another embodiment of the present invention there is provided a method of treating cancerous cells with alpha particles in an individual in need of such treatment comprising the step of administering a pharmacologically effective dose of an $^{225}Ac$ conjugate comprising a functionalized chelant having the structure

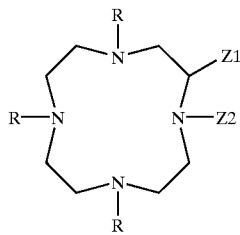

where R is independently $CHQCO2X$; Q is independently hydrogen; C1–C4 alkyl or (C1–C2 alkyl) phenyl; X is independently hydrogen; benzyl or C1–C4 alkyl; Z1 is $(CH2)_nY$ wherein n is 1–10 and Y is an electrophilic or nucleophilic moiety and Z2 is R; or, in the alternative, Z1 is hydrogen and Z2 is a peptide linker composed of 1–10 amino acids; said Y or said peptide linker covalently attached to an antibody or fragment thereof, or other biologic molecule; or a pharmaceutically acceptable salt thereof, complexed with $^{225}Ac$, wherein said antibody or fragment thereof, or other biologic molecule binds to said cancer cells, said $^{225}Ac$ or its daughters emitting said alpha particles into said cancerous cells, wherein said alpha particles cause a cytotoxic effect on said cancerous cells thereby effecting treatment of said individual.

In yet another embodiment of the present invention there is provided a method of treating cancerous cells with alpha particles in an individual in need of such treatment comprising administering a pharmaceutically effective dose of an $^{225}Ac$ conjugate comprising a functionalized chelant having the structure

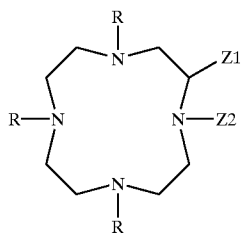

R and Z2 are $CH_2CO_2H$; and Z1 is $(CH_2)_nY$ wherein n is 1 to 10 and Y is an electrophilic or nucleophilic moiety; said Y covalently attached to a monoclonal antibody; or a pharmaceutically acceptable salt thereof; complexed with $^{225}Ac$; binding said monoclonal antibody to said cancerous cells; internalizing said $^{225}Ac$ within said cancerous cells, and emitting said alpha particles from said $^{225}Ac$ or its daughters, said alpha particles remaining within said cancerous cells, wherein said alpha particles cause a cytoxic effect on said cancerous cells thereby effecting treatment of said individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
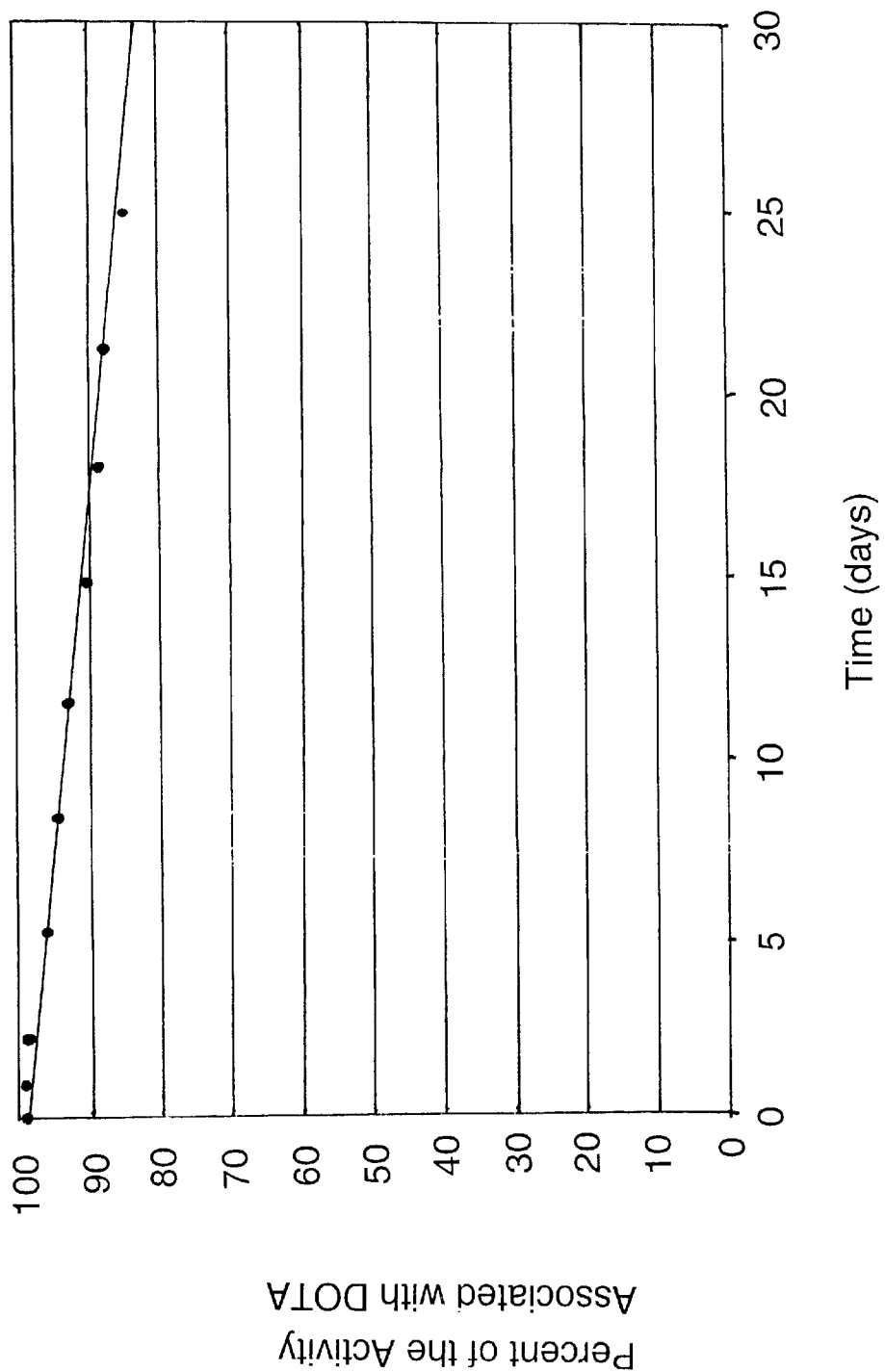
FIG. 1 shows the dissociation rate of $^{225}Ac$-DOTA.

In one embodiment of the present invention there is provided an $^{225}$Ac complex comprising a functionalized chelant compound having the structure

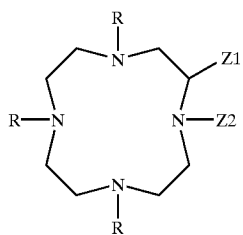

where R is independently CHQCO2X; Q is independently hydrogen; $C_{1-4}$-alkyl or ($C_{1-2}$-alkyl) phenyl; X is independently hydrogen; benzyl or $C_{1-4}$-alkyl; Z1 is $(CH_2)_nY$ wherein n is 1–10 and Y is an electrophilic or nucleophilic moiety and Z2 is R; or, in the alternative, Z1 is hydrogen and Z2 is a peptide linker composed of 1–10 amino acids; said Y or said peptide linker covalently attached to an antibody or fragment thereof, or other biologic molecule with the proviso that when R and Z2 are $CH_2CO_2H$, Z1 is not $CH_{(1-6)n}Y$ wherein Y comprises a para-substituted phenyl group, said phenyl substituent having a free end group comprising $-NO_2$, $-NH_2$, $-NCS$, $-COOH$, $-OCH_2COOH$, $-OCH_2COOH$, $NHCOCH_2Br$ or $NHCOCH_2I$; or a pharmaceutically acceptable salt thereof; complexed with $^{225}$Ac. A representative example of the functionalized chelant has R as $CH_2CO_2H$, Z1 as hydrogen and Z2 as the peptide linker.

In another embodiment of the present invention there is provided a method of treating cancerous cells with alpha particles in an individual in need of such treatment comprising the step of administering a pharmacologically effective dose of an $^{225}$Ac conjugate comprising a functionalized chelant having the structure

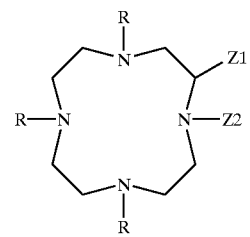

where R is independently CHQCO$_2$X; Q is independently hydrogen; C1–C4 alkyl or (C1–C2 alkyl) phenyl; X is independently hydrogen; benzyl or C1–C4 alkyl; Z1 is $(CH_2)_nY$ wherein n is 1–10 and Y is an electrophilic or nucleophilic moiety and Z2 is R; or, in the alternative, Z1 is hydrogen and Z2 is a peptide linker composed of 1–10 amino acids; said Y or said peptide linker covalently attached to an antibody or fragment thereof, or other biologic molecule; or a pharmaceutically acceptable salt thereof, complexed with $^{225}$Ac, wherein said antibody or fragment thereof, or other biologic molecule binds to said cancer cells, said $^{225}$Ac or its daughters emitting said alpha particles into said cancerous cells, wherein said alpha particles cause a cytotoxic effect on said cancerous cells, thereby effecting treatment of said individual.

In an aspect of this embodiment the structure may comprise those substituents on the chelant such that R and Z2 are $CH_2CO_2H$ and Z1 is $(CH_2)_nY$. An example of such a chelant is 2-(p-isothiocyanatobenzyl)-1,4,7,10-tetraazocyclododecane-1,4,7,10-tetra acetic acid. The nucleophilic or electrophilic moieties may be p-isothiocyanatobenzene, maleimides, vinylpyridine or NHS esters. The antibody may be IgG or a monoclonal antibody including an internalizing antibody which delivers the generator into the cancerous cells. Representative examples of such internalizing monoclonal antibodies are HuM195, J591, B4 and 3F8. The method of this embodiment may be used to target either disseminated cancers or solid tumor cancers. Representative examples of such cancers are prostate cancer, lymphoma, leukemia, neuroblastomas, breast cancer and ovarian cancer. Pharmaceutical compositions of the $^{225}$Ac conjugate and a pharmaceutical carrier may also be administered by the methods disclosed herein.

In yet another embodiment of the present invention there is provided a method of treating cancerous cells with alpha particles in an individual in need of such treatment comprising administering a pharmacologically effective dose of an $^{225}$Ac conjugate comprising a functionalized chelant having the structure

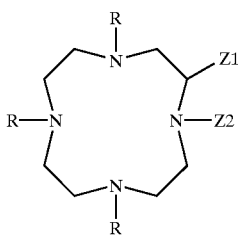

wherein R and Z2 are $CH_2CO_2H$; and Z1 is $(CH_2)_nY$ wherein n is 1 to 10 and Y is an electrophilic or nucleophilic moiety; said Y covalently attached to a monoclonal antibody; or a pharmaceutically acceptable salt thereof; complexed with $^{225}Ac$; binding said monoclonal antibody to said cancerous cells; internalizing said $^{225}Ac$ within said cancerous cells, and emitting said alpha particles from said $^{225}Ac$ or its daughters, said alpha particles remaining within said cancerous cells, wherein said alpha particles cause a cytoxic effect on said cancerous cells thereby effecting treatment of said individual. The conjugates, moieties, monoclonal antibodies and cancers of this embodiment may be those as disclosed supra.

The following definitions and abbreviations are given for the purpose of understanding the present invention. Any terms not expressly defined herein should be given their clear and ordinary meaning in the art.

As used herein, the term "$^{225}Ac$ complex" is a functionalized or bifunctional chelant complexed with $^{225}Ac$ radionuclide.

As used herein, the term "$^{225}Ac$ conjugate" refers to an $^{225}Ac$ complex that is covalently attached to a biological molecule.

As used herein, the term "individual" means any mammal, preferably a human.
Ab=antibody or MAb=monoclonal antibody
BFC=bifunctional chelant;
DOTA=1,4,7,10 tetraazacyclododecane-1,4,7,10-tetraacetic acid;
DOTA-NCS=2-(p-isothiocyanatobenzyl)-1,4,7,10-tetraazacyclododecane-1,4,7,10-tetraacetic acid;
MEO-DOTA-NCS=α-(5-isothiocyanato-2-methoxyphenyl)-1,4,7,10-tetraazacyclododecane-1,4,7,10-tetraacetic acid.
TMMA=tetramethyl ammonium acetate buffer; Sephadex C-25 resin is a cation exchange resin, sold by Pharmacia Inc.;
EDTA=ethylenediamine tetraacetic acid;
DTPA=diethylenetriamine pentaacetic acid;
TETA=1,4,8,11-tetraazacyclotetradecane-1,4,8,11-tetraacetic acid;
DOTPA=1,4,7,10-tetraazacyclododecane-1,4,7,10-tetra propionic acid
TETPA=1,4,8,11-tetraazacyclotetradecane-1,4,8,11-tetra propionic acid;
DOTMP=1,4,6,10-tetraazacyclodecane-1,4,7,10-tetramethylene phosphonic acid.

Compounds of the present invention, pharmaceutically acceptable salt thereof and pharmaceutical compositions incorporating such, may be conveniently administered by any of the routes conventionally used for drug administration, e.g., orally, topically, parenterally, or by inhalation. The compounds of the present invention may be administered in conventional dosage forms prepared by combining the compound with standard pharmaceutical carriers according to conventional procedures. The compounds of the present invention may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well known variable. The carrier(s) must be "acceptable" in the sense of being compatible with the other ingredients of the formulation and not deleterious to the recipient thereof.

The pharmaceutical carrier employed may be, for example, either a solid or a liquid. Representative solid carriers are lactose, terra alba, sucrose, talc, gelatin, agar, pectin, acacia, magnesium sterate, stearic acid and the like. Representative liquid carriers include syrup, peanut oil, olive oil, water and the like. Similarly, the carrier may include time delay material well known in the art such as glyceryl monosterate or glyceryl disterarate alone or with a wax. A wide variety of pharmaceutical forms can be employed. When a liquid carrier is used, the preparation will be in the form of a syrup, emulsion, soft gelatin capsule, sterile injectable liquid such as an ampule or nonaqueous liquid suspension.

Compounds of the present invention may be administered parenterally, i.e., by intravenous, intramuscular, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques Compounds may also be administered by inhalation, e.g., intranasal and oral inhalation administration. Appropriate dosage forms for such administration, such as aerosol formulation or a metered dose inhaler may be prepared by conventional techniques well known to those having ordinary skill in this art.

It will also be recognized by one of skill in this art that the optimal quantity and spacing of individual dosages of a compound of the present invention, or a pharmaceutically acceptable salt thereof, will be determined by the nature and extent of the condition being treated and that such optimums can be determined by conventional techniques. Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of the present invention may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

The methods of the present invention may be used to treat any individual. Most preferably, the methods of the present invention are useful in humans although any mammal may be treated.

Generally, as described herein, actinium-225 is complexed to a cyclic tetraazadodecane chelant having the following structure:

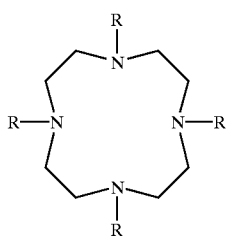

where R is independently CHQCO2X; Q is independently hydrogen; C1–C4 alkyl or (C1–C2 alkyl) phenyl and X is independently hydrogen; benzyl or C1–C4 alkyl complexed with 225Ac. In this form, the chelant is a simple chelant, however, attaching a sidechain provides bifunctionality to the compound. A reactive functional group can be attached to either the side chain or elsewhere in the ring structure as shown in the structure

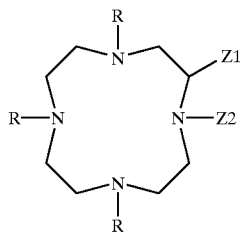

where R is as defined in Formula I and Z1 is (CH2)nY wherein n is 1–10 and Y is an electrophilic or nucleophilic moiety and Z2 is R; or, in the alternative, Z1 is hydrogen and Z2 is a peptide linker composed of 1–10 amino acids where Y and the peptide linker are covalently attached to an antibody or fragment thereof, or other biologic molecule; or a pharmaceutically acceptable salt thereof, complexed with $^{225}$Ac. The side chain and/or reactive functional group allow the second class of chelants to be covalently conjugated to an antibody, peptide, growth factor, cytokine, vitamin or other biomolecule. Examples of such moieties include p-isothiocyanatobenzene, maleimides, vinylpyridine, and NHS esters.

The $^{225}$Ac conjugates prepared from the bifunctional chelants in the present invention can be prepared by first forming the complex and then binding the biological molecule. Alternatively, the process may involve first conjugation of the ligand to the biological molecule and then the formation of the complex with $^{225}$Ac. Any suitable process that results in the formation of the $^{225}$Ac conjugates of this invention is within the scope of the present invention.

The $^{225}$Ac complexes and conjugates described herein are some of the most potent cytotoxic agents known. The $^{225}$Ac complexes and conjugates described have a wide application for the treatment of diseases such as cancer. They can be either alone or in combination with other biomolecules as in the case of pre-targeting. The bifunctional chelates of DOTA can be used for specific targeted alpha particle therapy. Conjugated with biomolecules, these DOTA bifunctional chelates of actinium-225 are designed for specific cell targeting, particularly disseminated cancers or solid tumor cancers.

The following examples are given for the purpose of illustrating various embodiments of the invention and are not meant to limit the present invention in any fashion.

EXAMPLE 1

Method of Preparation of $^{225}$Ac Complexes and Conjugates

The preparation of the $^{225}$Ac complexes involves a 2-step labeling method to prepare mCi amounts of Ac-225 (and Lu-177, In-111) labeled DOTA-NCS species at pH 4.5–5 in acetate buffer at 55–60° C. for 30 min. in high yield (95% +8%, n=36); subsequently, the [Ac-225]DOTA-NCS is mixed with IgG in carbonate buffer at pH 8.5–9 at 37° C. for 30 min. The final product is purified by size exclusion chromatography using a 10 mL BioRad 10DG column and 1% HSA. Typical reaction yields are 10%±5% (n=41) which yield sufficient amounts of Ac-225 labeled drug for these studies. Constructs thus prepared are assayed using established ITLC methods that quantify labeled IgG, free [Ac-225]chelate and unbound Ac-225 and cell-based immunoreactivity assays (25). HPLC analyses are not routine as a consequence of the low specific activities of the products.

Complexes between $^{225}$Ac and simple chelants of formula I are used as they are following quality control procedures and sterile filtration. The fraction of radioactivity associated with the antibody was then determined. The g emission counting was performed using a 3–inch×3-inch NaI well crystal utilizing the g emission of $^{225}$Ac decay product 221Fr (half-life of 4.8 min.) at 218 KeV. Counting was carried out half an hour after sample preparation.

EXAMPLE 2

Method for Determining Yield and Stability of $^{225}$Ac Complexes and Conjugates Thereof 100% human serum (Sigma Chemical Co., St. Louis, Mo.), 100% mouse serum and 25% human serum albumin (Swiss Red Cross, Bern, Switzerland) was used to determine stability of the $^{225}$Ac complexes and conjugates. Aliquots in serum are mixed with diethylenetriaminepentaacetic acid (DPTA) (Aldrich Chemical Co., Milwaukee, Wis.). ITLC was utilized with either a 10 mM EDTA or 10 mM NaOH/ 9% NaCl solvent system and ITLC SG strips (Gelman Science Inc., Ann Arbor, Mich.) to assess the complexation and conjugation efficiency of the chelants. The ITLC strips were analyzed by gas ionization detection with an Ambis 4000 (Ambis, San Diego, Calif.).

EXAMPLE 3

Labeling of Simple Chelants Including DTPA, TETA, DOTPA, TETPA, DOTA and DOTMP: Yields and Stability Approximately, 200 $\mu$Ci of $^{225}$Ac solution was mixed with 10 $\mu$l of 50 mM of a ligand solution (such as DOTA) and pH was adjusted to about 6–6.5 with 33 $\mu$l of 3 M ammonium acetate. The reaction was kept in a water bath at 37° C. for completion in 2 hours. Reaction yield was monitored using 10 mM NaOH/9% NaCl solvent. Then, 10 $\mu$l of 77.5 mM Yttrium chloride solution was added to react with excess chelants for 30 minutes. There are two reasons for adding the 1.5 fold excess Yttrium: 1) if $^{225}$Ac complex is not stable, Yttrium will replace $^{225}$Ac c, and 2) Yttrium will react with chelants and make a final solution at metal excess. The excess metal will be held on a C-25 purification column and the radiometal complex can pass through the column. Therefore, the purified solution should contain a 1:1 metal to ligand ratio for the stability studies.

Each reaction solution was purified through a 1 ml C-25 column using a 5 ml of normal saline as eluting buffer. The first 2.5 ml elution was collected for the stability study. The activity in the eluate and the activity retaining on the column were measured using a dose calibrator 20 hours after purification. Surprisingly, although DTPA, TETA, DOTPA and TETPA showed complete complexation of $^{225}$Ac before the yttrium was added, all the $^{225}$Ac in these solutions were retained on the column as would be expected for free $^{225}$Ac. The DTPA, TETA, DOTPA and TETPA complexes are therefore unstable and were not studied further. The percentage of $^{225}$Ac activity eluted from the column for $^{225}$Ac-DOTA was 98.7% and for $^{225}$Ac-DOTMP 78.6% demonstrating stable complexation by these two chelants.

Long-term in vitro stability of the $^{225}$Ac-DOTA complex was tested by mixing 100 μl of the purified sample with 900 μl of 25% human serum. The $^{225}$Ac-DOTA and solution was incubated at 37° C. and sampled periodically over the course of 30 days. The samples were analyzed by ITLC. The dissociation rate of $^{225}$Ac-DOTA is shown in FIG. 1. The graph demonstrates that 85% of the metal remains complexed after 1 month, which is 3 half-lives for $^{225}$Ac.

EXAMPLE 4
Preparation of $^{225}$Ac-HuM195 Conjugate
Preparation of $^{225}$Ac Complex:

An aqueous solution of the bifunctional chelant DOTA-NCS (20 μl; 10 mg/ml) was mixed with the $^{225}$Ac chloride solution (100 μl; 9.0 μCi/μl,) in 1.5 M HCl. The pH was adjusted to about 4.5 using the TMMA buffer (100 μl, 0.2 M, pH about 6). Reaction mixture was incubated at about 50° C. for one hour. ITLC analysis of the reaction mixture demonstrated that the 99.1% of the activity was complexed by the chelant.

Conjugation of the $^{225}$Ac Complex with the HuM195 Antibody

HuM195, a humanized anti-CD33 antibody that recognizes an antigen expressed on leukemia cells, was used for these studies. A solution of HuM195 (200 μl, 5 mg/ml) was added to the $^{225}$Ac complex solution (130 μl) prepared as described. Ascorbic acid (20 μl, 150 g/L) was added as a radioprotection agent. The pH was adjusted to about 8.5 using a NaHCO3 buffer (150 μl, 0.1 M, pH=8.7). The molar ratios of the reactants used were as follows: DOTA-NCS/$^{225}$Ac=4193; DOTA-NCS/HUM195=43; and HUM195/$^{225}$Ac=97. After 70 minutes incubation at 35° C. DTPA (20 μl, 10 mM) was added to complex any remaining radiometal that was not incorporated into DOTA-NCS. This step increases the purity of the radiolabeled protein. The resulting solution was loaded onto an Econo-Pack 10 DG gel filtration column. The radiolabeled protein was separated from contaminating small molecular weight components (DTPA-$^{225}$Ac and unconjugated DOTA-NCS-$^{225}$Ac) by eluting with a 1% v/v human serum albumin (HSA) solution in 0.9% saline. The percentage of the radiometal that was bound to the antibody was determined by g emission counting of the collected fraction and the column and comparing that to the original starting activity. It was determined that 10.4% of the $^{225}$Ac complex was coupled to HuM195 antibody. The purity of the radiolabeled protein fraction was determined to be 92% by ITLC, demonstrating that the BFC can be covalently bound to a biomolecule.

Stability of $^{225}$Ac-HuM195-DOTA

The purified $^{225}$Ac-HuM195-DOTA was assessed for stability in 100% human serum at 37° C. The solution was sampled at varying time points over the course of 9 days and was analyzed by ITLC. The assay demonstrated the conjugate is stable with 87% of the $^{225}$Ac still complexed to the HuM195-DOTA conjugate at the end of the assay. The stability of the $^{225}$Ac-DOTA chelate is measured on the antibody under conditions similar to those expected in vivo. [225Ac]DOTA-HuM195 construct is compared to a similarly prepared [177Lu]DOTA-Hum195 construct as a standard, in 100% human serum, 100% mouse serum, and 25% human serum albumin at 37° C. for 15 days.

Figure 2:
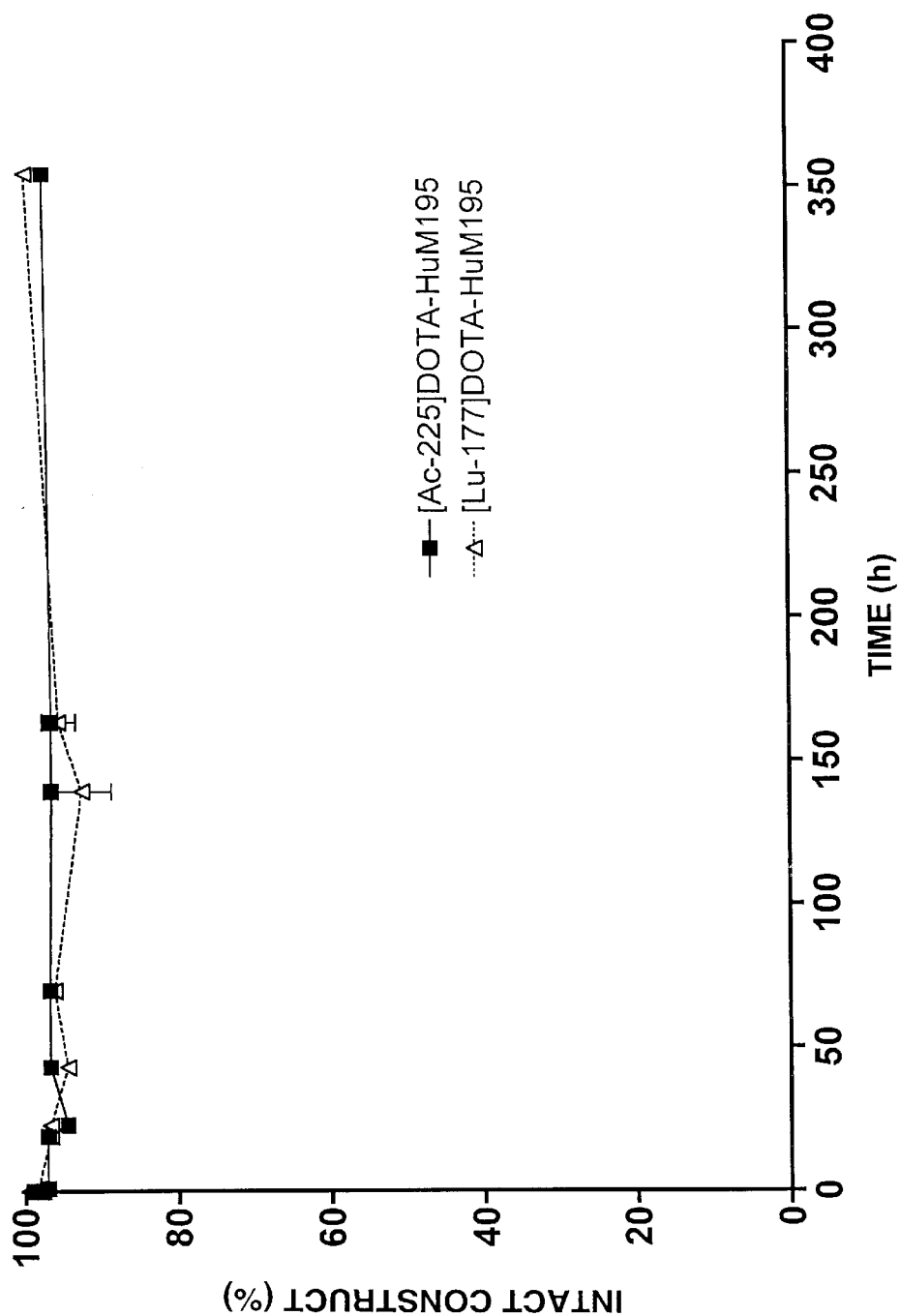
FIG. 2 shows the stability of [225Ac]DOTA-HuM195 (solid line, filled square) and [177Lu]DOTA-Hum195 (dashed line, open triangle) constructs in 100% human serum at 37° C. Values for the same two constructs in 100% mouse serum and 25% human serum albumin are identical and were omitted from this graph for clarity.

A 0.20 mL aliquot of either [225Ac]HuM195 or [177Lu] HuM195 is added to 4.0 mL of each of the three media. At each time point, 0.05 mL is removed from the six samples and mixed with 0.01 mL of 10 mM diethylenetriaminepentaacetic acid (DPTA) (Aldrich Chemical Co., Milwaukee, Wis.) for 15 min. at 37° C. After this 15 minute incubation period, an aliquot is removed and spotted (triplate) on instant thin layer chromatography paper impregnated with silica gel and developed with a 0.01 M EDTA solution. Strips are dried and counted four days later with a gas ionization detector. The [225Ac]HuM195 displayed stability similar to the [177Lu]HuM195 with less than a 5% loss of $^{225}$Ac from the IgG over 15 days. The results in all three conditions were similar (FIG. 2).

EXAMPLE 5
In vitro $^{225}$Ac-HuM195-DOTA Immunoreactivity

A cell based immunoreactivity assay (binding of labeled antibody to antigen excess) was used to determine the percentage of HuM195 that retained its immunoreactivity after conjugation and purification. The assay was conducted with antigen positive cells (HL60, available from American Tissue Culture Collection [ATCC]) and antigen negative cells (Daudi, ATCC).

The cells were centrifuged, the supernatant removed and the cells resuspended to a density of 108 cells/ml in 2% w/v bovine serum albumin in phosphate buffered saline, pH 7.2 (PBS). Aliquots of cell suspension (100 ml) were transferred to microcentrifuge tubes placed on ice to which purified $^{225}$Ac-HuM195-DOTA (3 ng) was added. The cell suspensions were incubated for 30 min, centrifuged and the supernatant containing any unbound $^{225}$Ac-HuM195-DOTA was transferred to a second microcentrifuge tube of cell suspension. The second tube was incubated on ice for 30 min. The first cell pellets were washed with PBS and the cells and washes saved for γ emission counting. The second set of cell suspensions were centrifuged, the supernatant removed and the pellets were washed with PBS. The set of supernate, cell pellets and washes were saved for counting. The percentage of radioactivity that was associated with the cells was then determined. The assay demonstrated that $^{225}$Ac labeled HuM195 antibody remained immunoreactive with 74% of the activity associated with the antigen positive cell line while the antigen negative cell retained 2% of the activity.

EXAMPLE 6
In vitro 225Ac-HuM195-DOTA Internalization

Biomolecules labeled with radioisotopes that emit alpha particles have increased cell killing ability when they are internalized. The $^{225}$Ac-generator constructs bound and internalized by tumor cells generate 221Fr, 217At, 213Bi, and 209Pb, yielding four net alpha-particle emissions per $^{225}$Ac decay. Critical to this generator approach is the retention of the daughter alpha-emitting atoms at or in the target cells. The HuM195, J591, and B4 antibodies internalize into HL60, LNCaP and Daudi cells, respectively, following binding (2,5,15–17) carrying with them the attached radionuclide.

The internalizing ability of the purified $^{225}$Ac-HuM195-DOTA was tested with HL60 cells. The cells were washed twice with complete media and then incubated for 20 min on ice in complete media containing 2% rabbit serum. The cells were washed twice with ice cold complete media and then resuspended in 5 ml of complete media at a density of 5×106 cells/ml. After placing the cell suspension on ice purified $^{225}$Ac-HuM195-DOTA (15 ng) was added. After mixing a sample of the sample of the cell suspension as taken and the rest of the cell suspension was placed into a 37° C. incubator. At various time points samples of the cell suspensions were taken. The samples were centrifuged, the supernatant removed and the cells washed twice with ice cold PBS. Stripping buffer (50 mM glycine, 150 mM NaCl, pH 2.8) was added to the cells and allowed to incubate for 10 min at room temperature. The cells were centrifuged and the supernatant drawn off and saved for counting. The cell pellet was washed once with PBS and both the cell pellet and wash were saved for counting. The assay demonstrated that 50% of the activity was internalized in 5 hours.

The radionuclidic decay of $^{225}$Ac yields two daughter radionuclides 221Fr and 213Bi that can be monitored by gamma spectroscopy in these experiments. LNCaP cells (10E6 cells) are exposed to an antibody-to-antigen excess of [225Ac]J591 at 37° C. for 90 minutes (triplicate). The assay is performed in the presence of 2% human serum. The cells are pelleted and washed 3x with ice cold PBS. The outside surface-bound [225Ac]J591 is stripped from the pelleted cells with 1 mL 50 mM glycine/150 mM NaCl (Aldich Chemical Co., Inc., Milwaukee, Wis.), pH 2.8, at 24° C. for 10 minutes.

Figure 3A:
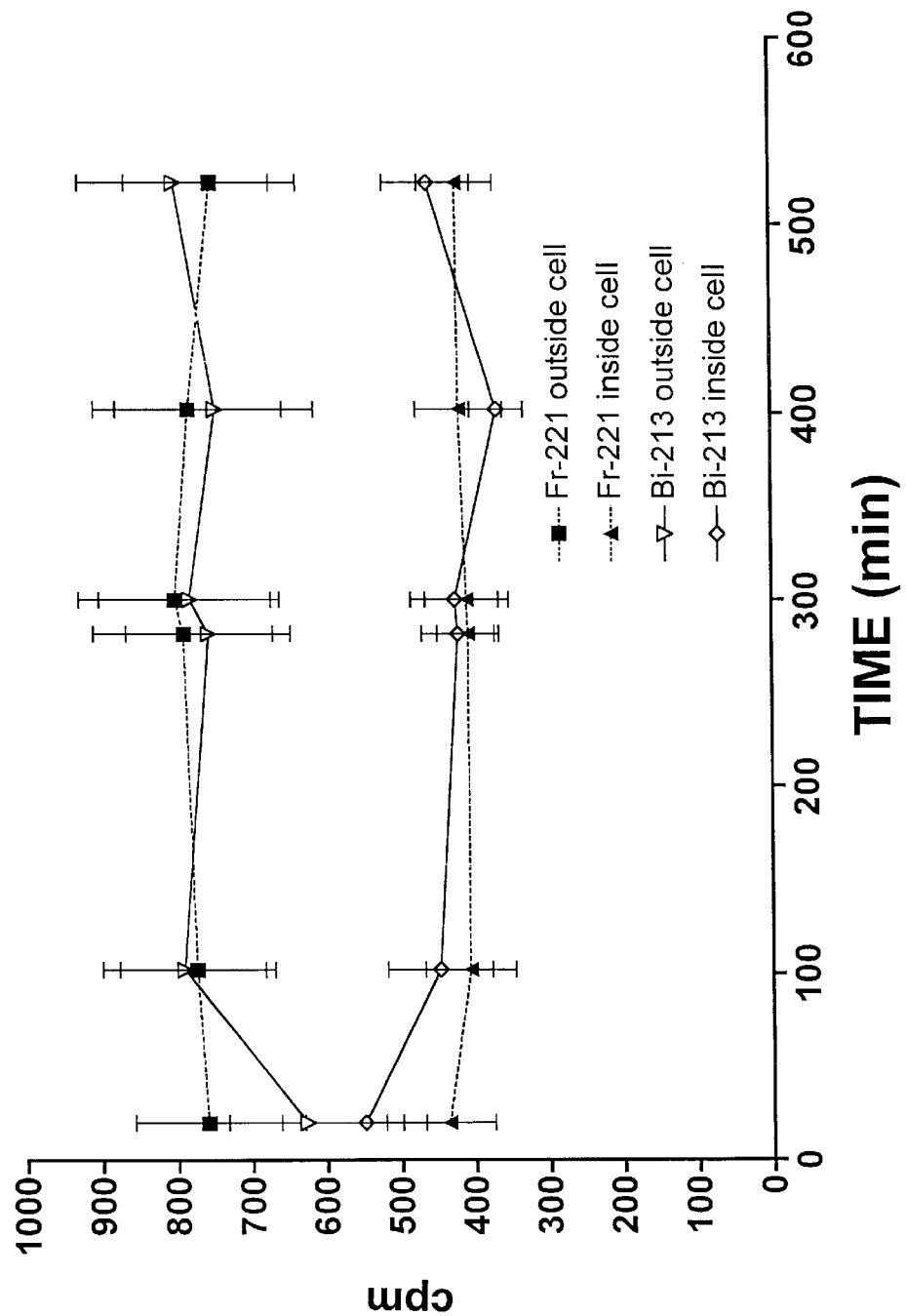
FIG. 3A shows the internalization and retention of [225Ac]J591/213Bi/221Fr in LNCaP cells in vitro. $^{221}Fr$ found outside the cell or surface bound (dashed line, filled squares); 221Fr internalized within the cell (dashed line, filled triangle); $^{213}Bi$ internalized within the cell (solid line, open diamond). $^{225}Ac$ that is internalized or is outside the cell is determined after 300 min. when secular equilibrium is established and the $^{213}Bi$ and $^{221}Fr$ curves converge

These analyses of the internalized generators show that initially there is a greater than equilibrium level of $^{221}$Fr and $^{213}$Bi present in the cell (FIG. 3A). This would indicate that $^{225}$Ac localized within the tumor cell results not only in daughters that remained there, but also some fraction of the decay products of the $^{225}$Ac bound to the outer cell membrane result in daughters that translocated into the cell interior. Therefore, there is more $^{221}$Fr and $^{213}$Bi and, hence, presumably the very short-lived $^{217}$At, radionuclides inside the cell than could be accounted for by $^{225}$Ac (at secular equilibrium) alone, demonstrating both accumulation and retention of the generator and its products. The remaining fraction of the cell surface bound [225Ac]IgG decay daughters may be held at the cell surface or released into the surrounding media.

EXAMPLE 7
In vivo $^{225}$Ac-HuM195-DOTA Internalization

The pharmacology of the generator constructs is determined in vivo in a xenograft prostate cancer model. Pharmacological analysis of $^{225}$Ac daughter is performed in vivo by injecting 12025 Beq of [225Ac]J591 (1.85 GBq/g) or 12025 Beq of [225Ac]HuM195 (irrelevant control) intraperitoneally in two groups (n=12 per group) of male athymic nude mice (Taconic, Germantown, N.Y.) bearing a 3–4 week old LNCaP intramuscular tumor xenograft. Mice from each group are sacrificed at days 2 and 3, respectively and the tumors, blood, and other tissues removed and immediately counted with a Packard Cobra Gamma Counter using two energy windows as described.

Activity was measured in each tissue sample as this was the quantity of interest regarding the issue of daughter retention or redistribution. Measurement of cpm as a function of time with an energy discriminating automated gamma counter allows for rapidly and repeatedly measuring the varying activity levels of each sample to determine where there was a deficit or excess of $^{221}$Fr and $^{213}$Bi relative to $^{225}$Ac secular equilibrium levels. $^{221}$Fr has a 4.9 min half-life, a 218 KeV gamma emission with 12.5% abundance; $^{213}$Bi has a 45.6 min half-life, a 440 KeV gamma emission with 16.5% abundance. The counting efficiencies using the Packard Automated Gamma Counter for $^{221}$Fr (185–250 KeV window) and $^{213}$Bi (360–480 window) are 0.83 cpm/dpm and 0.63 cpm/dpm, respectively.

Figure 3B:
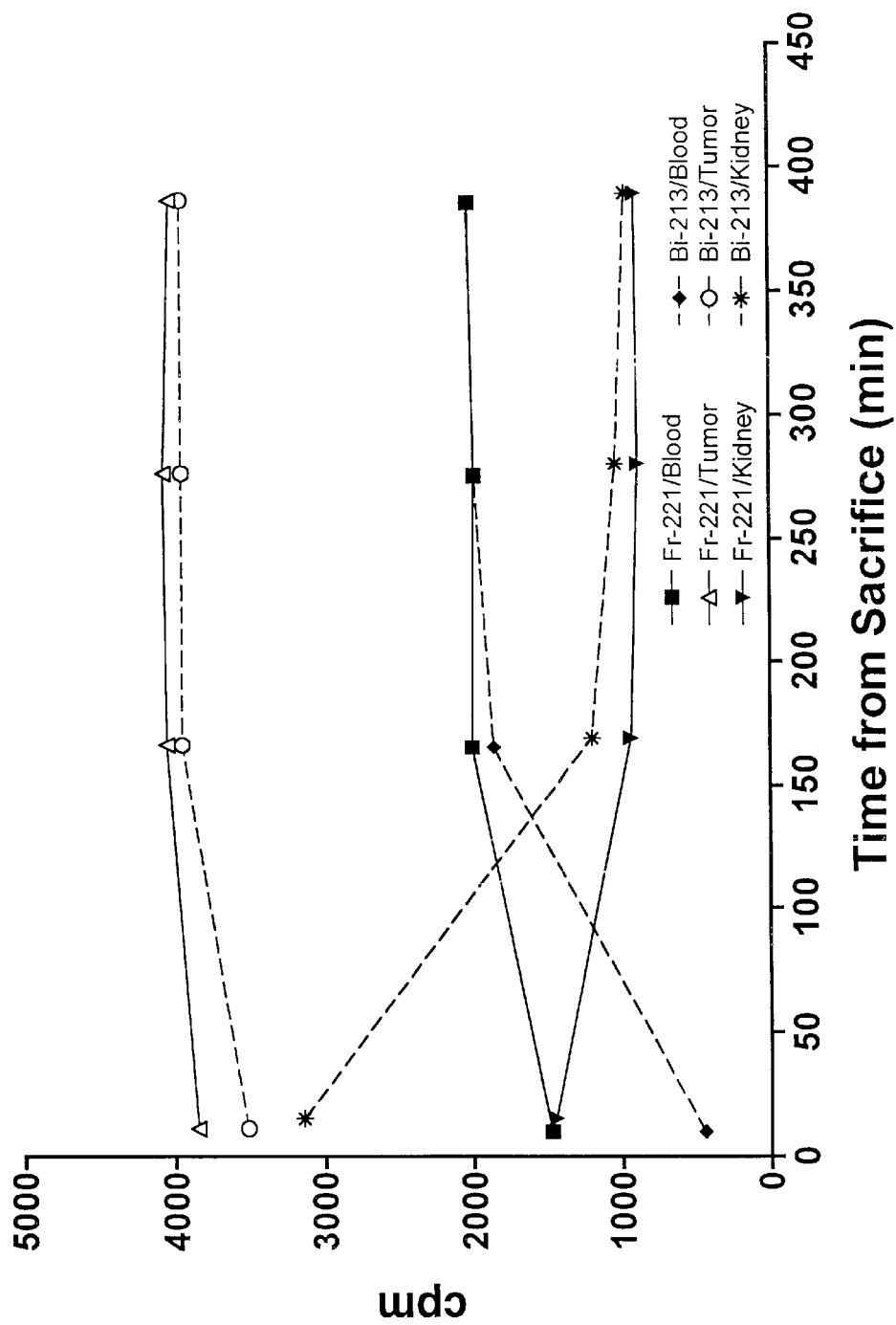
FIG. 3B shows the internalization and retention of [225Ac]J591/213Bi/221Fr tissues samples from one mouse in vivo. $^{221}Fr$ in the blood (solid line, filled squares); $^{221}Fr$ in the kidneys (solid line, filled triangle); $^{221}Fr$ in LNCaP tumor (solid line, open triangle). $^{213}Bi$ in the blood (dashed line, filled diamonds); $^{213}Bi$ in the kidneys (dashed line, asterisk); $^{213}Bi$ in LNCaP tumor (dashed line, open circle). $^{225}Ac$ that is internalized or is outside the cell is determined after 300 minutes when secular equilibrium is established and the $^{213}Bi$ and $^{221}Fr$ curves converge.

12% and 16% of the injected dose of [225Ac]J591 is localized in the tumor per gram at 2 days and 3 days, respectively after subtraction of control [225Ac]HuM195, and demonstrates a 3- to 4-fold increase in specific drug uptake at the tumor compared to non-specific control. Tumor samples (average of n=3) counted within 6–12 minutes of sacrifice, 2 days after drug injection showed activity levels of $^{221}$Fr and $^{213}$Bi, 96% and 89% of the $^{225}$Ac equilibrium levels, respectively. The actinium and daughters remain stable at the tumor as indicated in FIG. 3B. These measurements, however, represent a composite value of tumor cell internalized and surface bound [225Ac]J591 and its decay daughters. The daughters produced on the tumor cell's outer membrane surface are likely to be rapidly transferred away to eventually find their way to other sites including the kidneys and intestine (see Tables 1 and 2).

EXAMPLE 8
Toxicity of $^{225}$Ac Constructs

Figure 4:
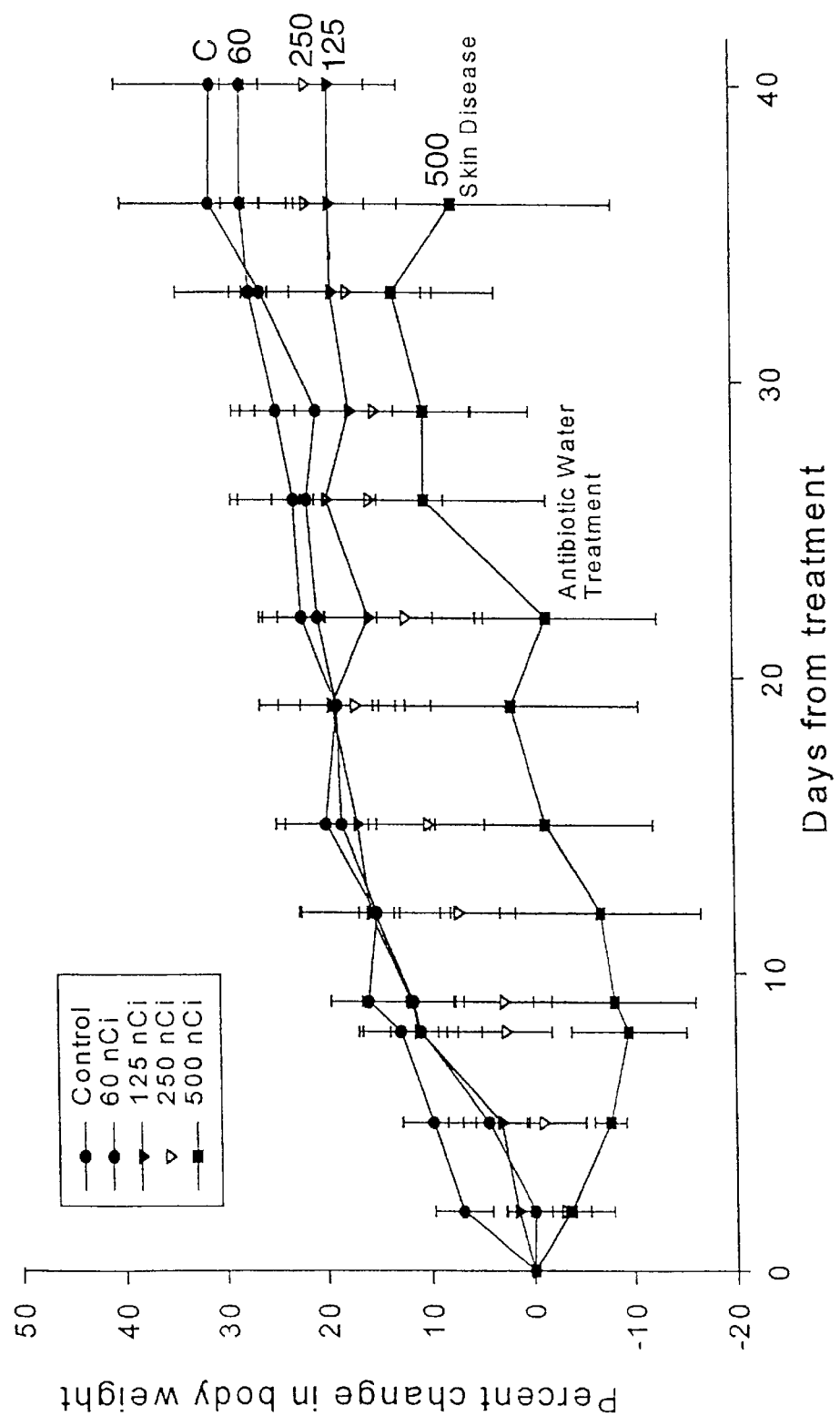
FIG. 4 shows the change in percent body weight vs. time following treatment with [225Ac]DOTA-B4.

A toxicity study over a 40 day period was conducted using forty 6–8 week old female athymic nude normal mice (NCI, Frederick, Md.) separated into 5 groups (n=8 per group). Four of the groups of mice were injected i.p. with 0.5 mL of 500, 250, 125, or 60 nCi of [225Ac]DOTA-B4 and a control group with an equivalent dose of unlabeled B4 IgG. Appearance, activity, weight, and tissue samples (liver, spleen, intestine, bone, muscle, kidney, lung and heart) were monitored for effects due to $^{225}$Ac toxicity. FIG. 4 shows the change in % body weight vs. time following treatment. Injection of 1000 nCi of [225Ac]B4 was lethal in all animals. Toxic effects were absent in the groups of animals receiving doses below 500 nCi while animals receiving 500 nCi experienced a greater than 10% loss of body weight. The dose limiting organ was the gastrointestinal tract. Normal animals tolerate a maximum single dose of 500 nCi of radiolabeled irrelevant IgG. Histological analysis of deceased mice showed gastrointestinal mucosal sloughing and bone marrow hyplasia, consistent with severe radiotoxicity.

Figure 5:
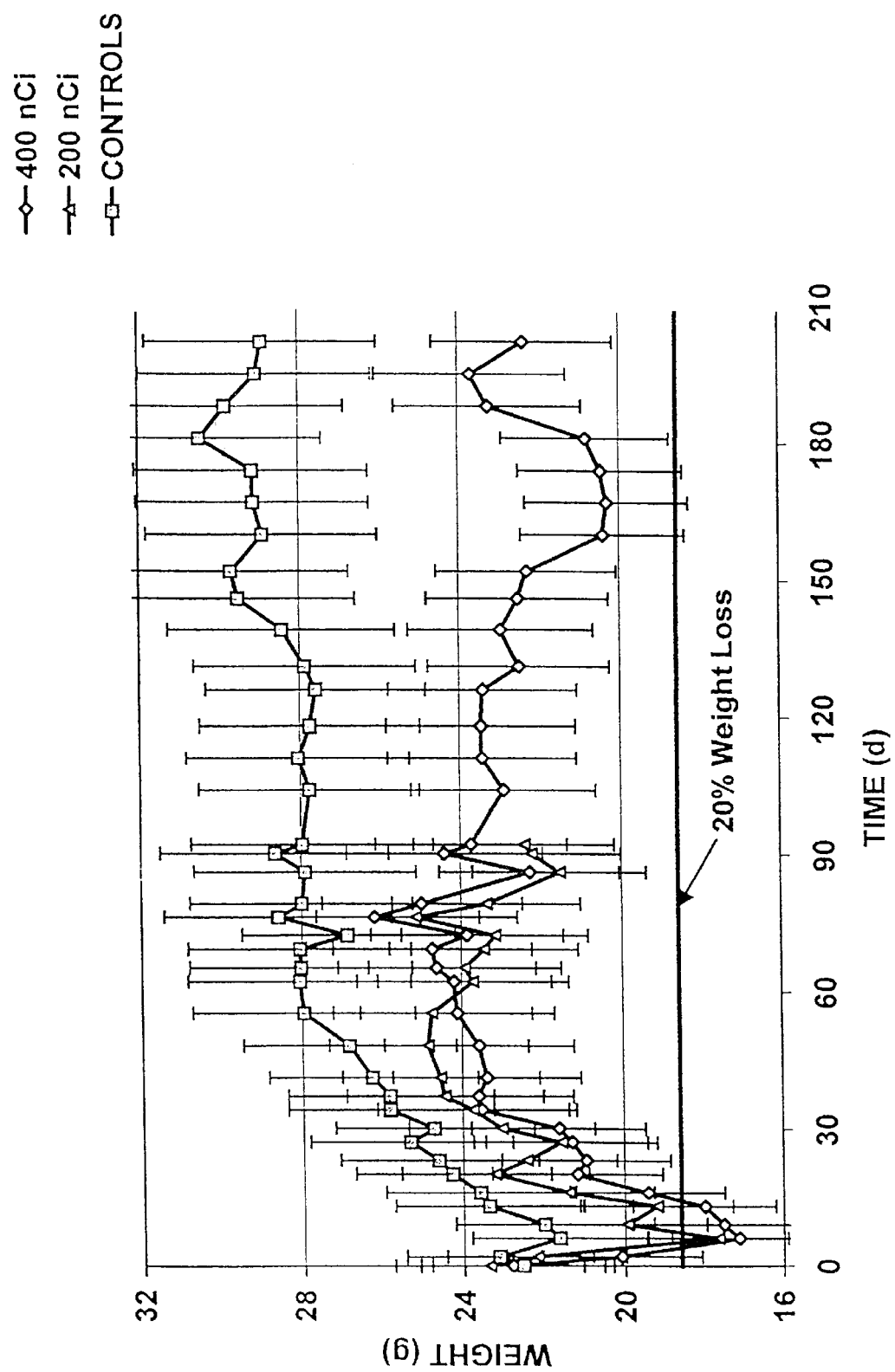
FIG. 5 shows the change in percent body weight vs. time following treatment with [225Ac]DOTA-HuM195.

A longer term toxicity study in forty normal mice (8 week old female balb/c mice from Taconic, Germantown, N.Y.) was conducted using [225Ac]DOTA-HuM195. Mice were separated into 10 groups (n=4 per group). Four of the groups received an i.p. injection of 400 nCi of [225Ac]DOTA-HuM195 and were held for 10, 30, 90, and 200 days before being sacrificed. Two of the groups received 200 nCi of [225Ac]DOTA-HuM195 and were held for 30 and 90 day periods. The remaining four groups served as untreated control animals and were held for 10, 30, 90, and 200 days before being sacrificed. Appearance, activity, weight, blood counts and blood chemistries were monitored for effects due to $^{225}$Ac toxicity relative to controls. FIG. 5 shows change in body weight vs. time following treatment. Dose levels of $^{225}$Ac in this study were chosen to examine toxicity below MTD to accompany the therapeutic studies.

Two male cynamologous monkeys (3–5 kg) were injected i.v. 9 months ago with an initial 0.002–0.005 mCi dose of [225Ac]DOTA-HuM195 per monkey and then 6 weeks later with a 0.017–0.020 mCi dose of [225Ac]DOTA-HuM195. Animals are followed by serial blood sampling and observation of activity and appearance as a function of time. Monkeys are 9 months out from injection and there has been no evidence of toxicity found. Hepatic, renal and hematopoietic function did not change.

One additional male cynamologous monkey (3–5 kg) was injected intrathecally (i.t.) 7 months ago with an initial 0.001 mCi dose of [225Ac]DOTA-3F8 (anti-GD2 antibody). Twelve weeks later the same monkey received a second i.t. injection of 0.0004 mCi of [225Ac]DOTA-3F8 and a second monkey was added to this study and received 0.005 mCi i.t. of [225Ac]DOTA-3F8 Animals are followed by serial blood sampling and observation of activity and appearance as a function of time. Monkeys are 7 and 3 months out, respectively from injection and there has been no evidence of toxicity found. Hepatic, renal and hematopoietic function were unchanged.

EXAMPLE 9
Biodistribution of $^{225}$Ac/$^{221}$Fr/$^{213}$Bi

J591 Biodistribution in LNCaP Tumor Bearing Mice

An [225Ac]DOTA-J591 biodistribution experiment was carried-out using a male athymic nude (8–12 weeks old) mouse (Taconic, Germantown, N.Y.) model with an i.m. xenograft of 5E6 LNCaP tumor cells in Matrigel (Becton Dickinson Labware, Bedford Mass.) implanted in the right hind leg. The tumors were allowed to grow for 4 weeks and then the mice were separated into two groups (n=12 per group). One group received approximately 0.55 mL of [225Ac]DOTA-J591 (350 nCi $^{225}$Ac on 0.0035 mg J591) and the other group received the irrelevant control [225Ac]DOTA-HuM195 (350 nCi 225Ac on 0.0026 mg HuM195) via i.p. injection. Three to four animals from each group were sacrificed at 48 h and 72 h post injection. Blood and tissue samples including: heart, kidneys, lung, spleen, liver, stomach, intestine, and tumor were harvested, weighed and counted using a Packard Cobra Gamma Counter (Packard Instrument Co., Inc., Meriden, Conn.) with two energy windows, $^{221}$Fr (185–250 KeV window) and $^{213}$Bi (360–480 window). The percent of the injected dose per gram of tissue (% ID/g) was determined by measuring the activity in 0.025 mg aliquots of each respective [$^{225}$Ac]mAb injectate in triplicate. After the initial 48 h time point data was analyzed, attention was focused on collection of blood, tumor, heart, kidney and small intestine samples as the need to rapidly sacrifice, harvest, and count was necessary in order to measure $^{221}$Fr in the samples.

Table I shows the combined data from the [225Ac]DOTA-J591 biodistribution at 48 h. Using known methods (28), values of A2(o)/A2(eq) were determined for each tissue sample. These values are the ratios of daughter/parent at the time of sacrifice. $^{221}$Fr/$^{225}$Ac and $^{213}$Bi/$^{225}$Ac ratios are very low in blood, demonstrating rapid clearance. Tumor ratios of $^{221}$Fr/$^{225}$Ac and $^{213}$Bi/$^{225}$Ac are 0.88±0.09 and 0.89±0.02, respectively. The kidneys and small intestine have high ratios, showing that the $^{221}$Fr and $^{213}$Bi deposit there. The percent injected dose/gram of $^{225}$Ac, $^{221}$Fr, and $^{213}$Bi in these key tissues were also tabulated and shown. $^{225}$Ac uptake in the liver was less than 10% in this system, showing stability of the chelated $^{225}$Ac.

Table II shows the combined data from the [225Ac] DOTA-HuM195 (targets CD33 in leukemia) biodistribution at 48 h including the ratios of daughter/parent at the time of sacrifice and the % injected dose/gram of $^{225}$Ac, $^{221}$Fr, and $^{213}$Bi in these key tissues. This antibody does not target LNCaP or other tissue in the mouse (2). The % injected dose/gram of tumor of $^{225}$Ac, $^{221}$Fr, and $^{213}$Bi were all lower in the control than in the [225Ac]DOTA-J591 biodistribution demonstrating specific tumor uptake. $^{225}$Ac uptake in the liver was less than 8% in this system.

TABLE 1

[Ac-225]DOTA-J591 48 hour distribution in mice

| Tissue | A2(o)/A2(eq) | | at sacrifice time % ID/g | | |
|---|---|---|---|---|---|
| | Fr-221 | Bi-213 | Fr-221 | Bi-213 | Ac-225 |
| Blood[a] | 0.05 | 0.15 | 0.23 | 0.68 | 0.31 |
| [b] | 0.05 | 0.10 | 0.28 | 0.37 | 4.55 |

TABLE 1-continued

[Ac-225]DOTA-J591 48 hour distribution in mice

| Tissue | A2(o)/A2(eq) | | at sacrifice time % ID/g | | |
|---|---|---|---|---|---|
| | Fr-221 | Bi-213 | Fr-221 | Bi-213 | Ac-225 |
| Tumor[a] | 0.88 | 0.89 | 15.6 | 15.7 | 17.6 |
| [b] | 0.09 | 0.02 | 4.36 | 3.78 | 3.86 |
| Heart[a] | 2.0 | 1.3 | 3.3 | 2.1 | 1.9 |
| [b] | 1.05 | 0.33 | 1.96 | 1.17 | 1.22 |
| Kidneys[a] | 6.0 | 3.8 | 45.6 | 30.0 | 7.7 |
| [b] | 1.27 | 0.71 | 16.86 | 10.77 | 1.40 |
| Sm. Int.[a] | 14.2 | 3.9 | 10.3 | 3.7 | 0.98 |
| [b] | 6.08 | 0.43 | 3.98 | 2.24 | 0.63 |
| Liver[a] | 0.97 | 0.82 | 9.1 | 7.9 | 9.6 |
| [b] | 0.05 | 0.03 | 2.18 | 2.14 | 2.41 |

[a]mean; [b]standard deviation

TABLE 2

[Ac-225]DOTA-HuM195 48 hour distribution in mice

| Tissue | A2(o)/A2(eq) | | at sacrifice time % ID/g | | |
|---|---|---|---|---|---|
| | Fr-221 | Bi-213 | Fr-221 | Bi-213 | Ac-225 |
| Blood[a] | 0.13 | 0.04 | 0.18 | 0.55 | 13.5 |
| [b] | 0.03 | 0.01 | 0.35 | 0.19 | 1.01 |
| Tumor[a] | 0.83 | 0.87 | 4.6 | 5.0 | 1.60 |
| [b] | 0.19 | 0.04 | 1.23 | 3.9 | 3.9 |
| Heart[a] | 1.6 | 0.99 | 6.1 | 3.9 | 3.9 |
| [b] | 1.30 | 0.21 | 4.73 | 0.72 | 0.29 |
| Kidneys[a] | 16.8 | 10.0 | 72.8 | 46.5 | 4.7 |
| [b] | 2.24 | 0.48 | 4.24 | 5.0 | 0.41 |
| Sm. Int.[a] | 13.3 | 4.0 | 18.7 | 6.3 | 1.6 |
| [b] | 3.85 | 0.14 | 3.67 | 0.46 | 0.14 |
| Liver[a] | 0.70 | 0.87 | 5.5 | 6.5 | 7.7 |
| [b] | 0.66 | 0.11 | 5.14 | 0.43 | 0.95 |

[a]mean; [b]standard deviation

In contrast to these two [225Ac]DOTA-IgG constructs, free $^{225}$Ac (acetate) injected into a mouse rapidly accumulates in the liver: 40%, 40%, 65% at 24 h, 48 h, and 120 h, respectively. This demonstrates that the $^{225}$Ac is retained by the DOTA chelate in vivo and is not leaking out of the complex and being taken-up by the liver.

In the [225Ac]HEHA-HuM195 construct in vivo in a normal mouse model (29) 40% of the injected dose per gram liver after 120 h was observed. This HEHA chelate has been described as leaky (26), losing $^{225}$Ac to the liver. The DOTA-IgG constructs shown in Tables 1 and 2 do not show this high degree of liver uptake (7.7 to 9.6%ID/g in our DOTA-IgG systems). Thus, if $^{225}$Ac leaked out of DOTA in vivo, it should accumulate in the liver as was observed with the $^{225}$Ac acetate and $^{225}$Ac-HEHA-IgG construct. Therefore, the $^{213}$Bi accumulation in the kidney must be from decay of daughters from nontargeted constructs.

EXAMPLE 10
225Ac-HuM195-DOTA Specific Activity and LD50

Figure 6:
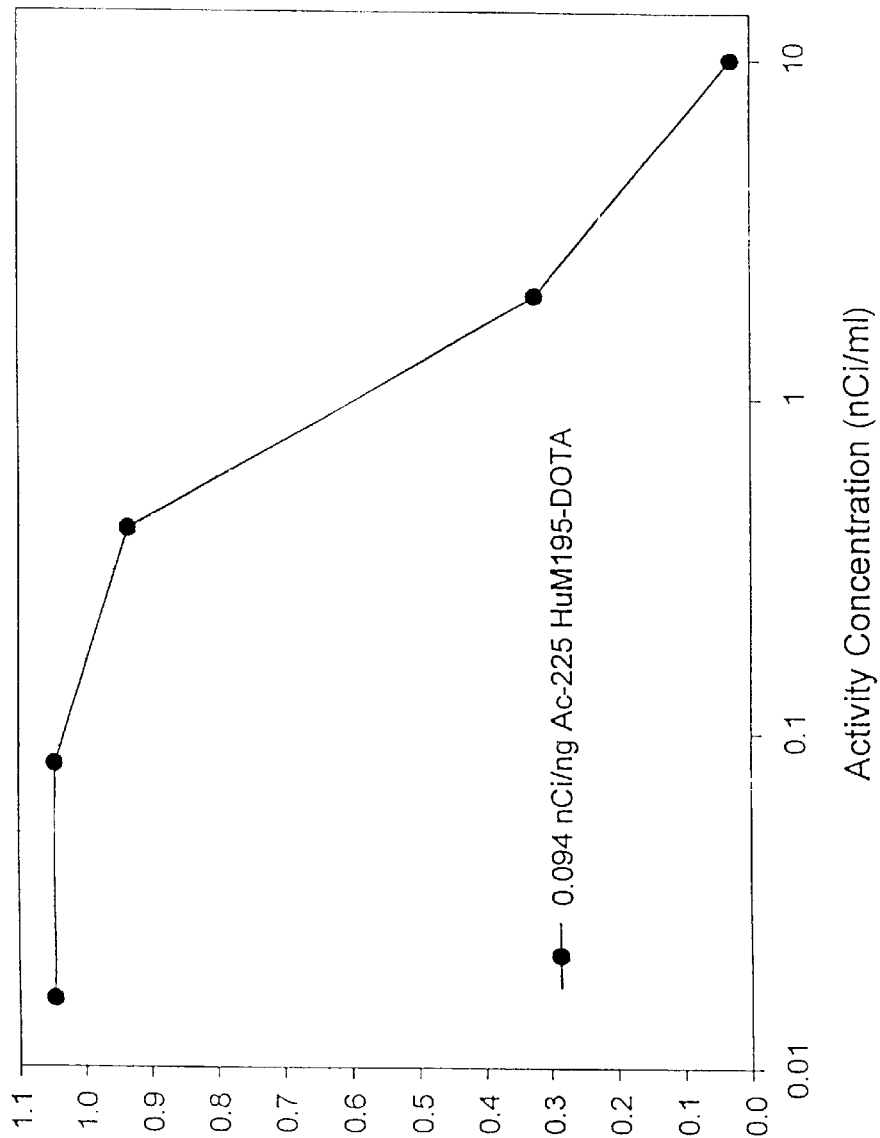
FIG. 6 shows 225Ac-HuM195-DOTA specificity and potency against HL60 cells in vitro as a function of specific activity and activity concentration.

The potency and specificity of 225Ac-HuM195-DOTA was then evaluated in-vitro as a function of specific activity and activity concentration (FIG. 6). A suspension of HL60 cells were washed twice with complete media and then dispensed into a 96 well cell culture plate in complete media supplemented with 2% human serum. The volume was 100 μl and the cells were at a density of 5×105 cells/ml. Next a serial dilution of purified $^{225}$Ac-HuM195-DOTA was added to the wells. The diluent was complete media and volume added was 100 µl. The starting activity was 10 nCi/ml, which was diluted 5-fold for each subsequent tube. The specific activity was 0.094 nCi/ng of antibody. The cells were incubated for 2 days at 37° C., following which tritiated thymidine was added (0.5 pC, in 50 il complete media/well). The cells were incubated at 37° C. for an additional 5 h, then harvested using a Combi Cell Harvestor (Skatron Instruments). Cell viability was determined by analyzing the degree of tritiated thymidine incorporated into the DNA of the treated cells relative to control cells. The LD50 is about 1.3 nCi/ml demonstrating the extreme potency of this reagent for killing a leukemic cell line, suggesting that $^{225}$Ac-DOTA conjugates are useful clinically as a way to irradiate target cells with alpha particles.

Specific killing of leukemia cells, lymphoma cells, breast carcinoma, prostate carcinoma, and ovarian cancer is observed at very small doses of generators. The generator system shows remarkable potency in vitro that is 1000- to 10000-fold enhanced relative to $^{213}$Bi constructs using the same leukemia, prostate, and lymphoma systems (2, 5, 14). This represents a significant multi-log increase in potency of the generator. The potency and specificity of [225Ac]IgG for killing single cancer cells is determined using 5E4 cells in 0.2 mL per well in 96 well plates. Serial dilutions of [225Ac]IgG are added (triplicate) to the cells to yield final activity in the wells ranging from 74 kBl/mL to 37E-6 kB q/mL. Non-specific killing is measured after target cells are blocked with a 100–10000-fold excess of unlabeled IgG before plating and subsequent addition of [225Ac]IgG.

These LD50 values range from 0.3 to 74 B q/mL (0.008 to 2 nCi/mL) and are approximately 100–25,000-fold lower than the previously published most potent cytotoxic agents, $^{213}$Bi alpha-particle emitting antibodies (2,5, 15). Table 3 shows a comparison of $^{213}$Bi and $^{225}$Ac in vitro cytotoxicity.

TABLE 3

Comparison of Bi-213 and Ac-225 In Vitro Cytotoxicity

| Construct | S.A. (Ci/g) | LD50 (pCi/mL) | Cells |
|---|---|---|---|
| [Ac-225]J591 | 0.17 | 90 | LNCaP |
| [Bi-213]J591 | 6.4 | 220,000 | LNCaP |
| [Ac-225]B4 | 0.13 | 60 | Ramos |
| [Bi-213]B4 | 42 | 280,000 | Ramos |
| [Ac-225]HuM195 | 0.24 | 8 | HL60 |
| [Bi-213]HuM195 | 8.4 | 200,000 | HL60 |

Controls at very low specific activities (in excess unlabeled antibody) do not show specific binding of the alpha-particle generators to the targets, and represent the non-specific cytotoxicity in the system used here. The LD50 values are 10- to 625-fold higher in the controls using excess unlabeled antibody (Table 4).

TABLE 4

| GENERATOR[1] | CELLS[1] | S.A.[2] (GBq/g) | LD$_{50}$ (Bq/mL) |
|---|---|---|---|
| [Ac-225]J591 | LNCaP(specific) | 6.3 | 3.3 |
|  | LNCaO(non-specific) | 0.063 | 330.0 |
| [Ac-225]B4 | Ramos(specific) | 4.8 | 2.2 |
|  | Ramos(non-specific) | 0.048 | 111.0 |
| [Ac-225]HuM195 | HL60 (specific) | 8.9 | 0.3 |
|  | HL60(non-specific) | 0.089 | 185.0 |

TABLE 4-continued

| GENERATOR[1] | CELLS[1] | S.A.[2] (GBq/g) | LD$_{50}$ (Bq/mL) |
|---|---|---|---|
| [Ac-225]3F8 | NMB7 (specific) | 1.5 | 3.7 |
|  | NMB7(non-specific) | 0.075 | 37.0 |
| [Ac-225]Herceptin | BT-474(specific) | 1.9 | 5.6 |
|  | SKOV (specific) | 3.3 | 74.0 |

[1]J591: murine IgG2A directed against PSMA, expressed on LNCaP human prostate carcinoma cells
B4: murine IgG1 directed against CD19, expressed on human Ramos lymphoma cells
HuM195: humanized IgG1 directed against CD33, expressed on human HL60 leukemia cells
3F8: murine IgG3 directed against GD2 expressed on NMb7 human neuroblastoma cells
Herceptin: humanized IgG1 directed against HER2, expressed on human BT-474 breast carcinoma cells and SKOV3 ovarian carcinoma cells
[2]Dilution of the generator with a 20-100-fold excess of antibody yields a low specific activity (S.A.) used as a non-specific killing control

EXAMPLE 11

In vivo $^{225}$Ac-J591-DOTA Efficacy Against LNCaP Tumor Cells

An intramuscular (i.m.) injection of 5E6 LNCaP tumor cells mixed with Matrigel results in a 100% tumor take rate in these 8–12 week old male nude mice; tumor growth in vivo is also confirmed and followed by measuring human serum prostate specific antigen (PSA) (5, 18, 19). Pre-therapy PSA values are 2, 3 and 5 ng/mL on 10, 10 and 12 days after implantation of tumor (three experiments of 37, 39 and 33 animals each). At the time the generator is administered on day 12 or 15, the tumors are characterized histologically as vascularized and encapsulated nodules each comprised of tens of thousands of cells (5).

Figure 7A:
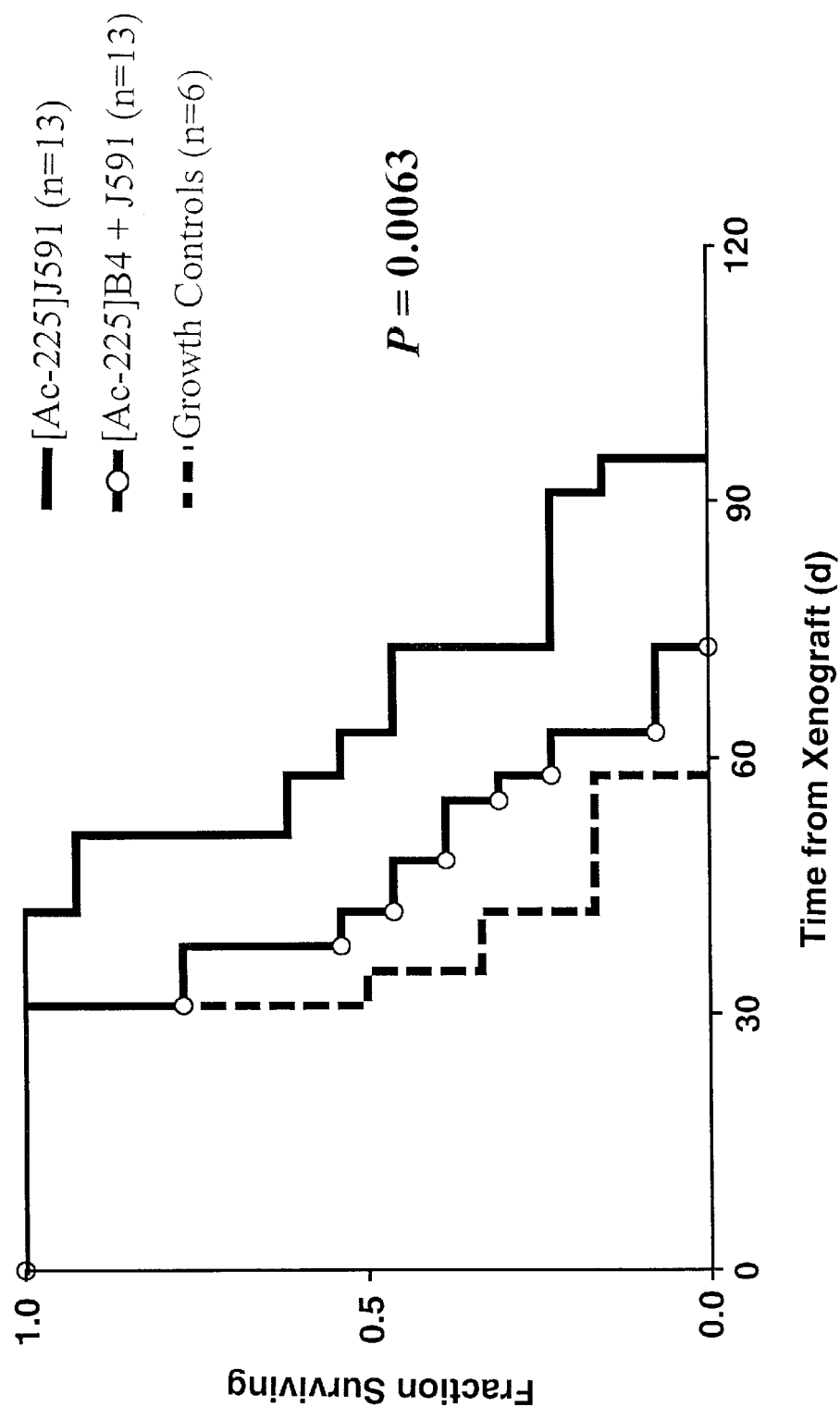
FIG. 7A shows a Kaplan-Meier plot of the fraction of mice surviving vs. time from xenograft for LNCaP xenografted mice treated with 7178 Bq[225Ac]J591 (black), 7178 Bq[225Ac]B4+J591 (solid line, open circles), and an untreated growth control (dashed line).

In one prostate tumor therapy study, a single nontoxic dose of the [225Ac]J591 generator on 15 day post-implantation significantly improves (P<0.006) median survival times of LNCaP xenografted mice relative to mice treated with [225Ac]B4 irrelevant control antibody mixed with unlabeled specific J591 (dual control) or untreated controls (FIG. 7A). In other experiments, the maximum tolerated dose (MTD) is determined to be 18.5 kBq (500 nCi) [225Ac]IgG as there is weight loss whereas animals that are injected with 37 kBq (1000 nCi) of [225Ac]IgG did experience lethal toxicity. Based on these studies, therapeutic doses were selected that are appproximately 40% of MTD. Two normal male cynamologous monkeys have been intravenously infused with a similar dose (based on weight) without toxicity. In this prostate cancer therapy experiment PSA is assayed day 12d post-tumor xenograft. Animals are subsequently arranged into groups with evenly distributed PSA values and treated 15d post-tumor implantation. PSA in remaining alive animals is measured on days 28, 42, 55, and 69 post xenograft. Animals are sacrificed when tumor area is ≧2.5 cm². All treatments are administered via intraperitoneal injection. Median tumor-free survival vs. time from tumor xenograft is evaluated using a log-rank test and plotted as a Kaplan-Meier survival curve. There is no significant difference in survival times between the dual control [225Ac]B4+J591 treated animals and untreated controls. The median survival time of untreated growth controls in this model is 33 days (n=15).

Figure 7B:
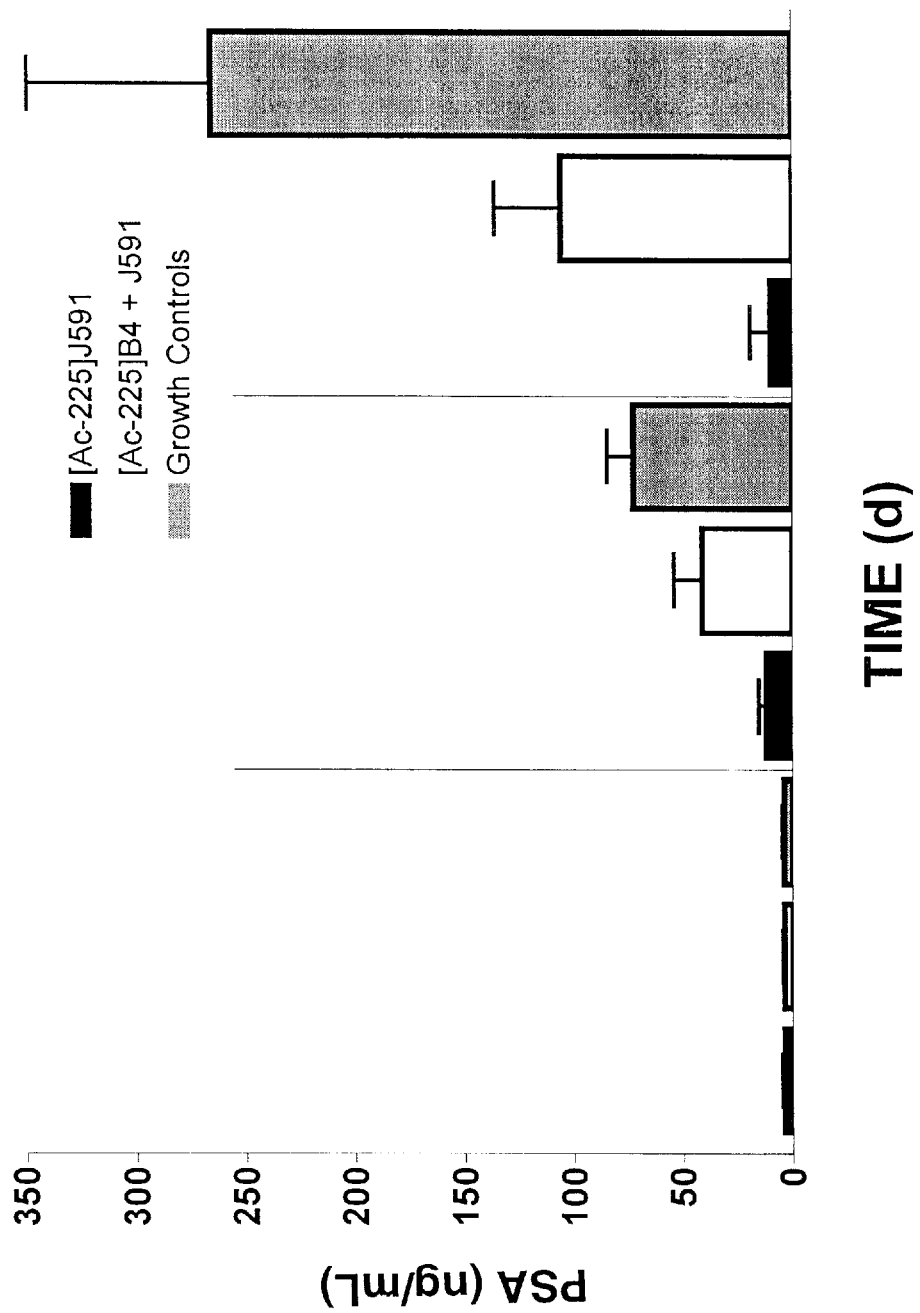
FIG. 7B shows the median serum PSA values at days 12, 28 and 42 for LNCaP xenografted mice treated on day 15 with 7178 Bq[225Ac]J591 (black), 7400 Bq[225Ac]B4+J591 (white), and untreated growth controls (gray) in therapeutic study. PSA values are evaluated using an unpaired t-test with two-tailed P-values (95% confidence limit) to analyze differences between study groups.

PSA is an important surrogate marker for prostate cancer burden and prognosis in humans (19). It can also be used in animal models with prostate cancer cell xenografts (5,18). Rising PSA predicts appearance of visible tumor and their death. PSA levels in tumor-bearing mice responded to the treatment in the experiment above (FIG. 7B). The mean and median pre-therapy PSA values measured on day 12 are not significantly different between the three groups of mice. However, on days 28 and 42, the PSA values of [225Ac] J591 treated animals are significantly lower than the PSA values for the dual control [225Ac]B4+J591 treated animals and untreated controls. There is no significant difference between the dual control [225Ac]B4+J591 treated animals and untreated controls at either time. Using GraphPad's Prism statistical software, the PSA values for individual mice were entered and analyzed. The day 42 PSA values yielded P=0.2814 (untreated growth control vs. dual controls ($^{225}$Ac-labeled irrelevant B4 co-mixed with unlabeled J591) using an unpaired t-test, two-tailed, 95% confidence interval. A similar analysis of day 42 data for [Ac-225]J591 vs. the dual controls groups yields P=0.0037; and [Ac-225]J591 vs. untreated growth control yields P=0.0008. A one-way ANOVA for all three groups at day 42 yielded P=0.0025.

Figure 7C:
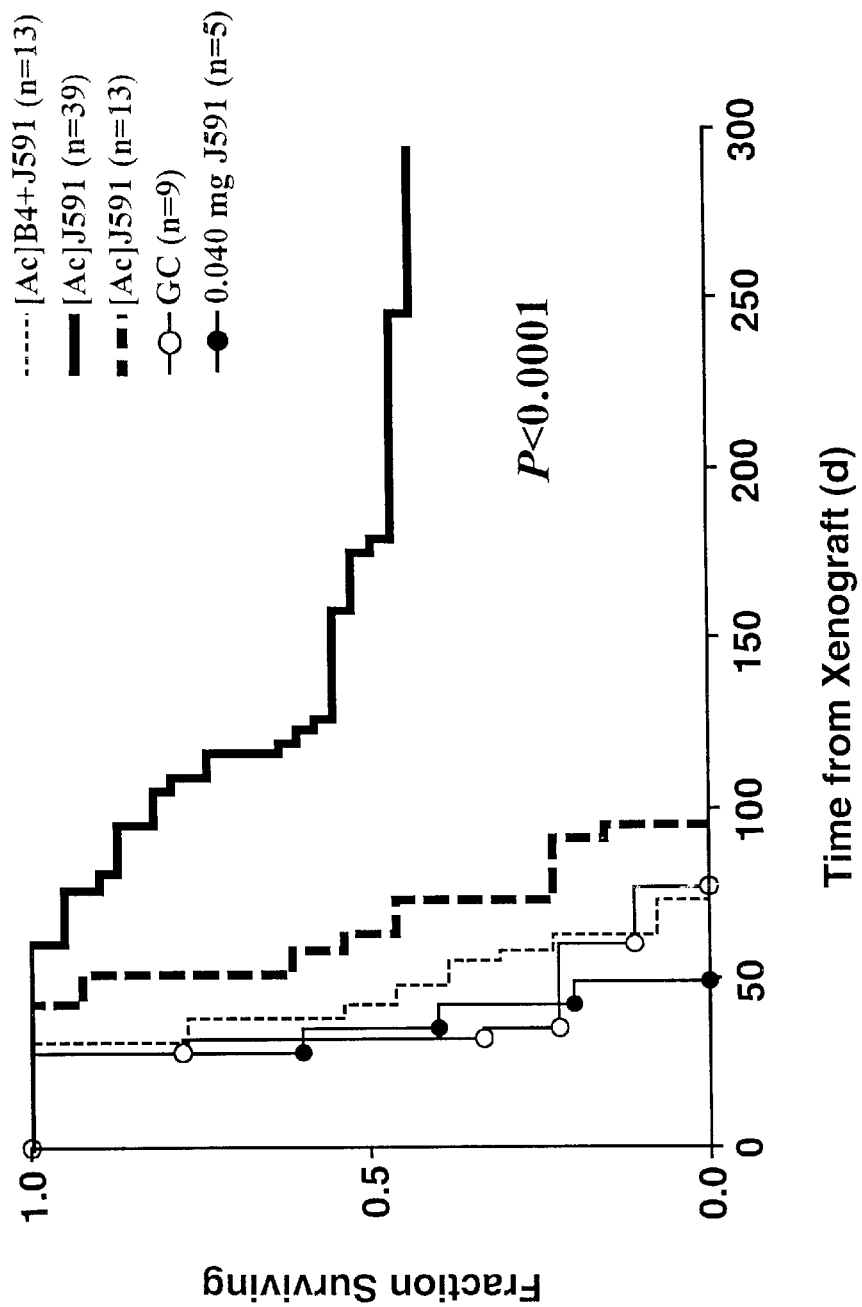
FIG. 7C shows the Kaplan-Meier survival plot of the fraction of mice surviving vs. time from xenograft in several therapy/control experiments in LNCaP model using a 7770 Bq dose of [225Ac]J591 on day 12 (heavy solid line) vs. a 7178 Bq dose of [225Ac]J591 on day 15 (heavy dashed line). Controls are a 7400 Bq dose of [225Ac]B4+J591 (small dashed line); 0.040 mg of unlabeled J591 (small solid line, closed circles); and untreated growth controls (small solid line, open circles). In the second therapy experiment PSA is assayed 10 days post-tumor xenograft and treatment begins 12 days post-tumor implantation. Live animals are assayed for PSA on days 26, 47, 76, 111, 181, and 284 post-xenograft.
Figure 7D:
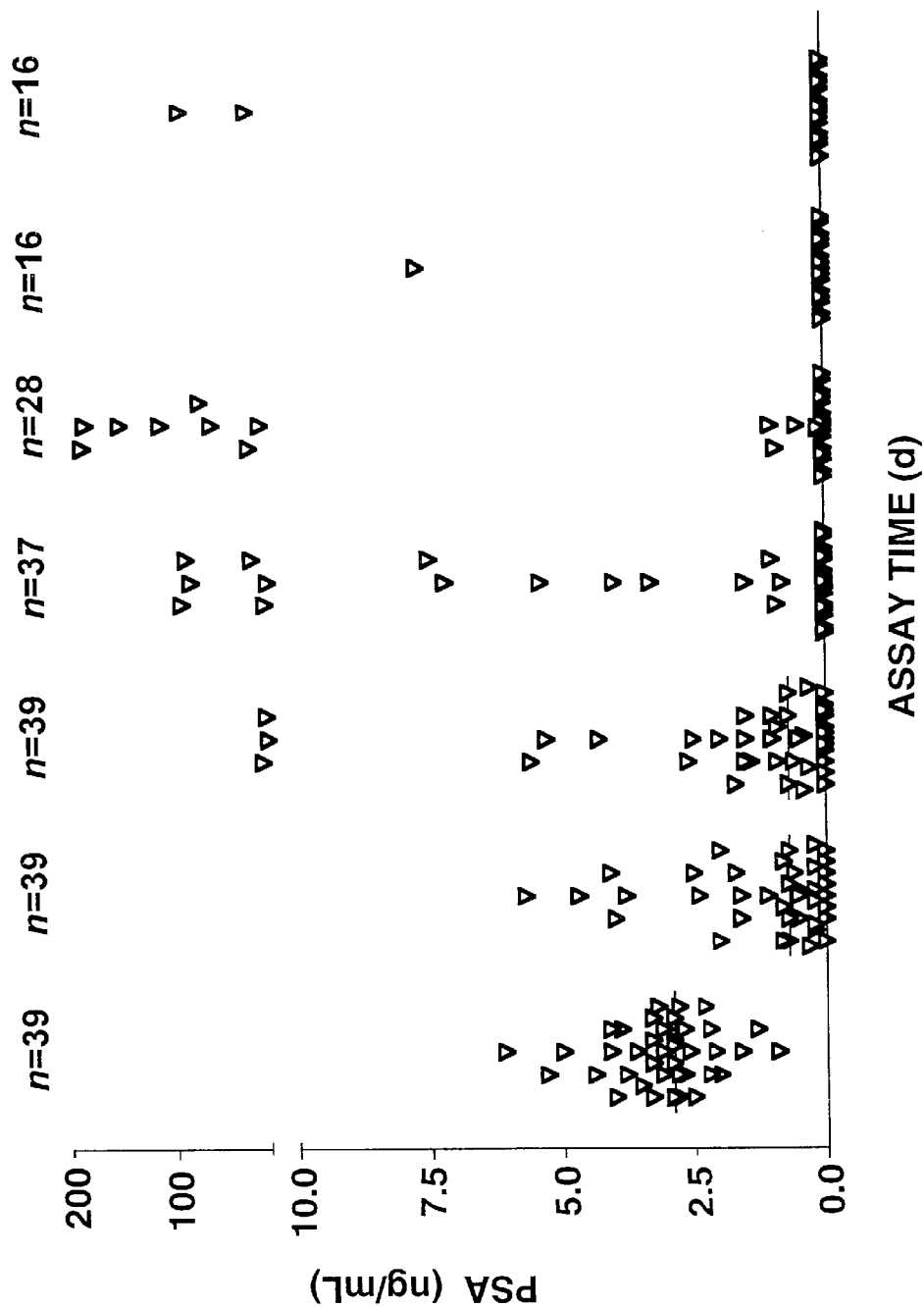
FIG. 7D shows the individual serum PSA values of the 39 mice treated with a 7770 Bq dose of [225Ac]J591 on day 12 in therapy experiment with LNCaP model. Median is marked with a solid line. PSA values are evaluated as described in FIG. 7B.

A single dose of [225Ac]J591 administered to 39 mice, 3 days earlier at 12 days after standard tumor xenograft, all bearing tumor as confirmed by PSA levels, results in cures and significantly improved (P<0.001) the median survival times of these mice to 158 days from 63 days in the mice treated in the earlier experiment (FIG. 7C). PSA values of the mice in this experiment are measured at days 10 (3 day pre-therapy), 26, 47, 76, 111, 181, and 284 and demonstrated rising PSA in the fraction of animals showing tumor progression and ultimately death; PSA decreases from pretherapy level in many of the animals over the course of treatment to low and undetectable levels prolonging survival and remains undetected in the 14 cured animals (FIG. 7D).

A durable complete response, i.e., no measurable PSA and no tumor, is observed in 36% of the 39 mice given a single treatment of [225Ac]J591. These mice survived at least 10 months and are apparently cured having no measurable PSA or evidence of tumor at the time of sacrifice at 293 days. Animals treated with unlabeled J591 (0.004 or 0.04 mg) 12 days post-implantation have no prolongation of median survival (37 days and 35 days, respectively, n=9).

The prostate therapy trials in mice demonstrate the efficacy of single, subtoxic doses of [225Ac]J591 generators in mice with established carcinomas. Comparison of treatment at 12 days and 15 days from xenograft (average PSA values of 3 and 5 ng/mL, respectively) in two separate experiments favored the earlier treatment time. The therapeutic efficacy is dependent on antibody specificity, the administration of the generator, and the treatment time after implantation.

EXAMPLE 12
In vivo $^{225}$Ac-B4-DOTA Efficacy Against Daudi Lymphoma Cells

Daudi lymphoma cells are disseminated into 8–12 week old female Scid mice via an intravenous (i.v.) injection of 5E6 Daudi tumor cells in the tail vein; mice experience a 100% tumor take rate in the model (20). In this lymphoma therapy experiment mice are treated 1 day post-tumor dissemination via intravenous injection. Animals are monitored for signs of illness and hind leg paralysis or inability to breathe or ambulate at which time they are sacrificed.

Figure 8A:
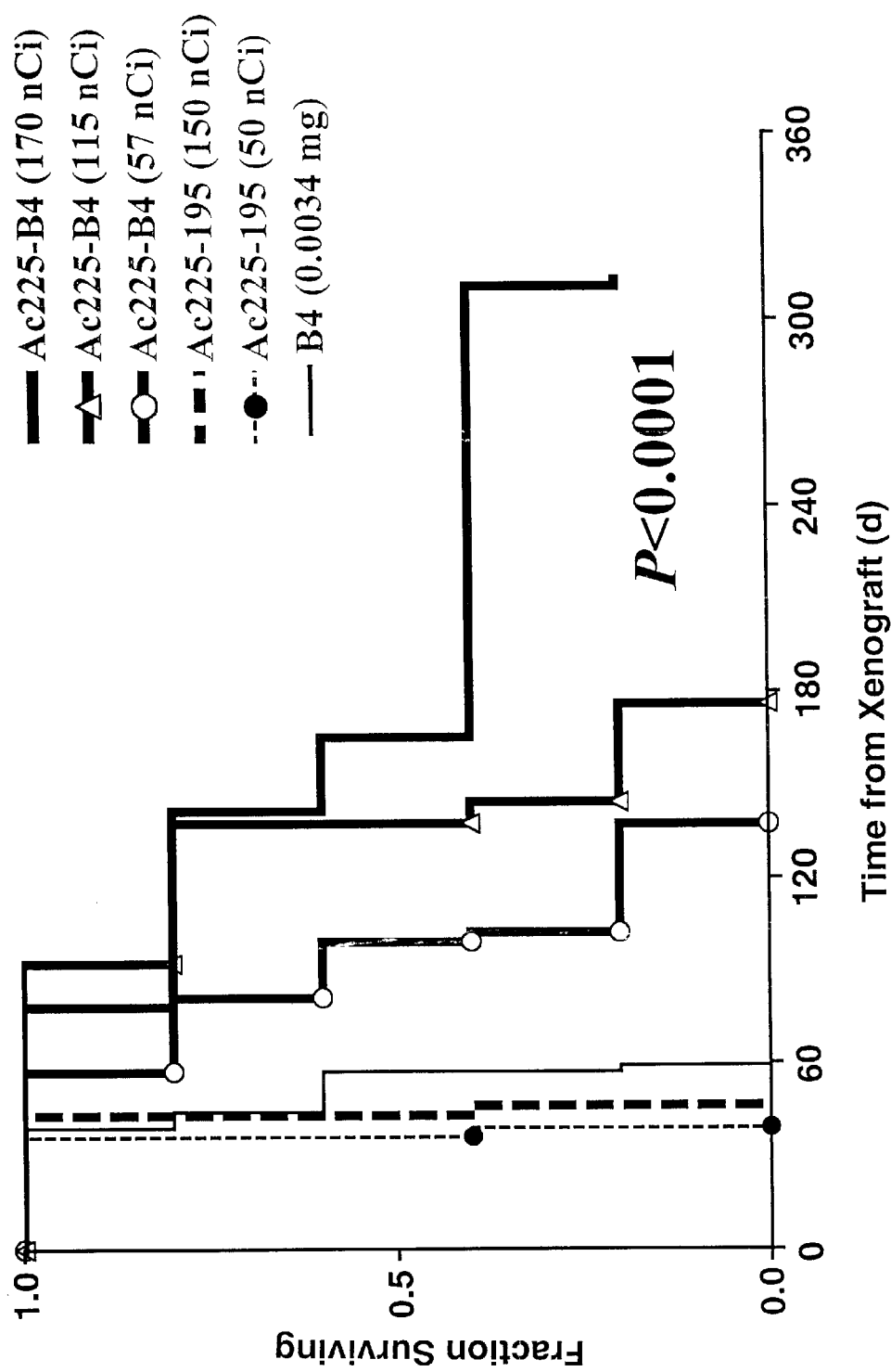
FIG. 8A shows a Kaplan-Meier survival plot of the fraction of mice surviving vs. time from xenograft for disseminated Daudi xenografted mice treated with single 6512 Bq (heavy solid line); 4255 Bq (heavy solid line, open triangles); or 2146 Bq (heavy solid line, open circles) doses of [225Ac]B4; Controls received a single 5550 Bq (heavy dashed line) or 1850 Bq (small dashed line, filled circles) doses of [225Ac]HuM195, or 0.0034 mg unlabeled B4 (small solid line). Statistical analysis is performed as in FIG. 7B.

In the first experiment with this disseminated model, mice are treated 1 day post-tumor dissemination with a single dose of labeled specific [225Ac]B4 at three different dose levels, irrelevant control [225Ac]HuM195 at two dose levels, or a mass of unlabeled B4 matching the antibody mass dose administered in the highest dose level radiolabeled groups. Control groups receiving the irrelevant [225Ac]HuM195 have median survival times from xenograft of 43 days and 36 days. Mice receiving 0.003 mg unlabeled B4 per mouse have a median survival time of 57 days from xenograft. The mice receiving a single injection of [225Ac]B4 show dose-related increases in median survival times from xenograft to 165, 137 and 99 days, respectively. The dose response of [225Ac]B4 is significant with P=0.05. The difference between the three specific treatment arms and the three controls (FIG. 8A) is significant P<0.0001.40% of mice treated at the highest dose are tumor-free at 300 days, although one animal is sacrificed tumor-free at 310 days.

Figure 8B:
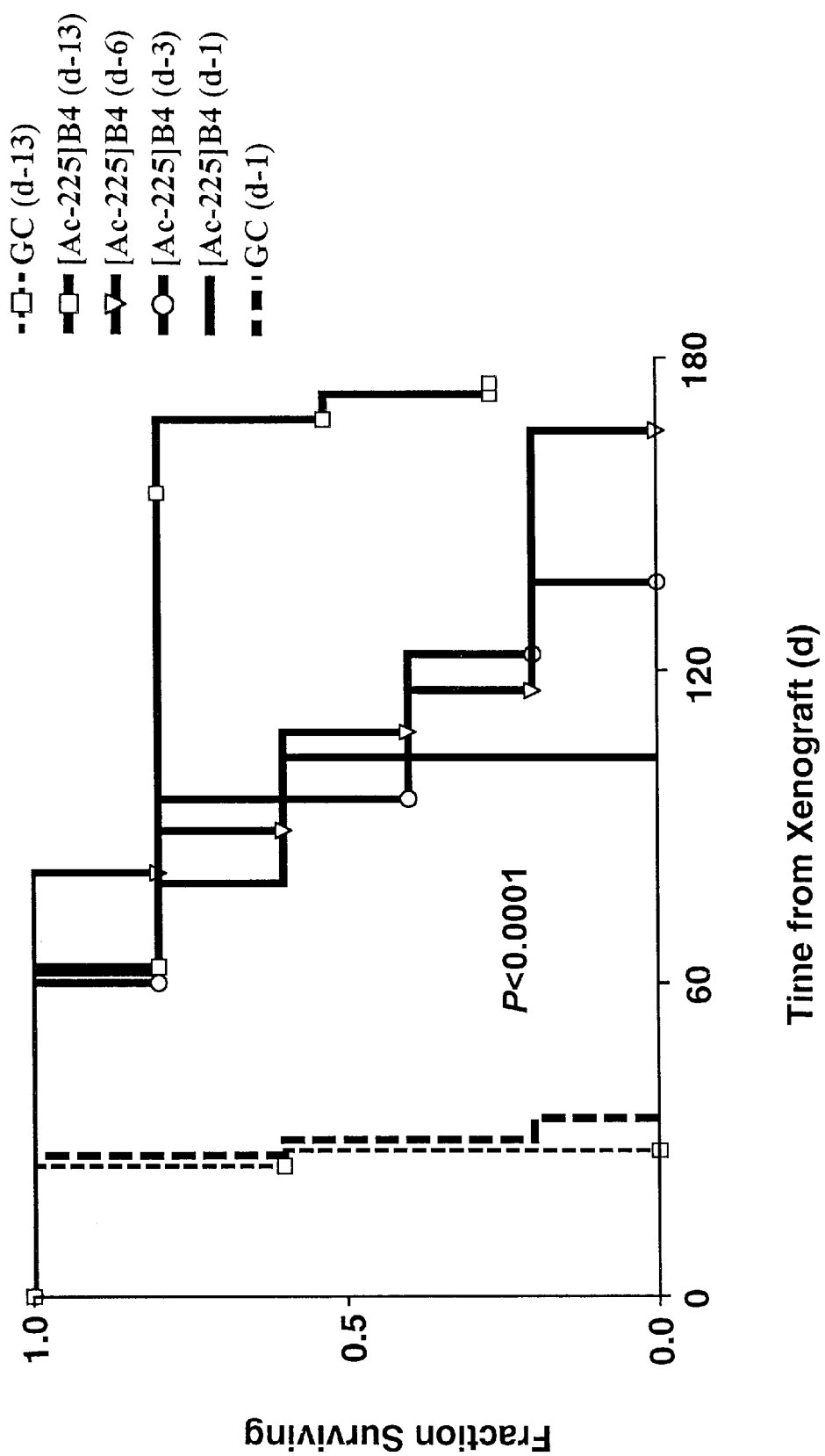
FIG. 8B shows the Kaplan-Meier survival plot of the fraction of mice surviving vs. time from xenograft for disseminated Daudi xenografted mice treated with single 6290 Bq doses of [225Ac]B4 on days 13 (solid line, open squares), 6 (solid line, open triangles), 3 (solid line, open circles), or 1 (solid line) after xenograft. Controls are untreated animals with xenografts initiated day 13 (small dashed line, open squares) or day 1 (large dashed line). Animals are monitored and statistical analysis is performed as in FIG. 7B.

The time of treatment from lymphoma dissemination is investigated in a similar experiment (FIG. 8B). In this lymphoma therapy experiment mice are treated with one dose on either day 1, 3, 6, or 13 post-tumor dissemination. Mice (n=15) receiving treatment on either day 1, 3 or 6 post tumor implantation with a single dose of [225Ac]B4 have similar prolongation of survival. Mice (n=5), receiving treatment with a single dose of [225Ac]B4, show a pronounced therapeutic effect as far out as 13 days post tumor dissemination and survive more than 165 days. Unlabeled B4 is minimally active in mice (n=5 per group) with median survival of 44 days and 40 days for mice treated with 0.002 mg or 0.20 mg, respectively and untreated growth controls (n=15) have a median survival time of 28 days from tumor dissemination (data not shown).

These lymphoma trials in mice demonstrate the efficacy of single, subtoxic doses of [225Ac]B4 generators in mice with a disseminated cancer. Therefore, in this model, while specificity and dose level are important factors in efficacy, the treatment time after tumor dissemination appears less relevant up to a time-point where it then is inversely related to activity. The later phenomena may be a result of geometry effects related to eradicating single cells and small clusters vs. larger aggregates of tumor cells.

The following references are cited herein:
1. J. L. Humm, L. M. Chin. Radiation Res. Vol. 134, pg. 143 (1993).
2. T. N. Nikula et al. Nucl. Med. Vol. 40, pg. 166 (1999).
3. J. G. Jurcic et al. Blood. Vol. 90(suppl), pg. 504a (1997).
4. M. R. Zalutshy, G. Vaidyanathan. Current Pharmaceutical Design. Vol. 6, No. 14, pg. 1433 (2000).
5. M. R. McDevitt et al. Can. Res. Vol. 60, pg. 6095 (2000).
6. A. M. Ballangrud et al., Can. Res. Vol. 61, pg. 2008 (2001).
7. M. R. McDevitt, R. D. Finn, G. Sgouros, D. Ma, D. A. Scheinberg. Appl. Rad. Isotopes. Vol. 50, pg. 895 (1999).
8. M. R. McDevitt, R. D. Finn, D. Ma, S. M. Larson, D. A. Scheinberg. J. Nucl. Med. Vol. 40, pg. 1722 (1999).
9. M. W. Geerlings Sr., F. M. Kaspersen, C. Apostolidis, R. Van Der Hout. Nucl. Med. Commun. Vol. 14, pg. 121 (1993).
10. M. R. McDevitt et al. European J. Nucl. Med. Vol. 25, pg. 1341 (1998).
11. D. Ma et al. paper presented at the 2000 International Chemical Congress of Pacific Basin Societies, Honolulu, Hi., Dec. 14, 2000.
12. M. R. McDevitt et al. J. Nucl. Med. Vol. 42, No. 5, pg. 316P (2001).
13. M. Miederer et al. J. Nucl. Med. Vol. 42, No. 5, pg. 315P (2001).
14. D. Ma et al. J. Nucl. Med. Vol. 41, No. 5, pg. 1175 (2000).
15. H. Liu et al. Can. Res. Vol. 58, pg. 4055 (1998).
16. P. M. Smith-Jones et al. Can. Res. Vol. 69, pg. 5237 (2000).
17. D. Ma et al. Leukemia, in press.
18. M. E. Gleave, J. -T. Hsieh, H. -C. Wu, A. C. von Eshenback, W. K. Chung. Can. Res. Vol. 52, pg. 1598 (1992).

19. J. M. Bidart et al. Clin. Chem. Vol. 45, No. 10, pg. 1695 (1999).
20. M. A. Ghetie et al. Blood. Vol. 83, No. 5, pg. 1329 (1994).
21. S. J. Kennel et al. Cancer Biotherapy and Radiopharmaceuticals. Vol. 15, No. 3, pg. 235 (2000).
22. I. A. Davis et al. Nucl. Med. & Biol. Vol. 26, pg. 581 (1999).
23. L. L. Chappell, K. A. Deal, E. Dadachova, M. W. Brechbiel. Bioconjugate Chem. Vol. 11, pg. 510 (2000).
24. K. A. Deal, I. A. Davis, S. Mirzadeh, S. J. Kennel, M. W. Brechbiel. J. Med. Chem. Vol. 42, pg. 2988 (1999).
25. McDevitt et al. J. Nucl. Med. Vol. 40, pgs. 166–176 (1999).
26. S. Mirzadeh et al. Radiochimica Acta. Vol. 60, No. 1 (1993).
27. McDevitt et al. J. Nucl. Med. Vol. 41, No. 5, pg. 116 (2000).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An $^{225}$Ac complex comprising a functionalized chelant compound having the structure

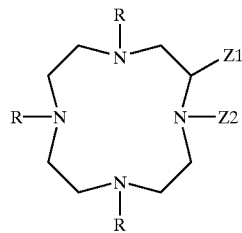

wherein R is independently —CHQCO$_2$X;
Q is independently hydrogen; —C$_{1-4}$-alkyl or —(C$_{1-2}$-alkyl) phenyl;
X is independently hydrogen; benzyl or —C$_{1-4}$-alkyl; and
Z1 is —(CH$_2$)$_n$Y wherein n is 1 to 10 and Y is an electrophilic or nucleophilic moiety and Z2 is R; or, in the alternative,
Z1 is hydrogen and Z2 is a peptide linker composed of 1–10 amino acids;
with the proviso that when R and Z2 are CH$_2$CO$_2$H, Z1 is not (CH$_2$)$_{(1-6)}$Y; wherein Y comprises a para-substituted phenyl group, said phenyl substituent having a free end group Comprising —NO$_2$, —NH$_2$, —NCS, —COOH, —OCH$_2$COOH, —OCH$_2$COOH, —NHCOCH$_2$Br or —NHCOCH$_2$I;
or a pharmaceutically acceptable salt thereof complexed with $^{225}$Ac;
further comprising an antibody or fragment thereof, a growth factor or a cytokine that is covalently attached to Y or to said peptide linker.

2. The $^{225}$Ac complex of claim 1, wherein R is CH$_2$CO$_2$H, Z1 is hydrogen and Z2 is a peptide linker composed of 1–10 amino acids.

3. A method of treating cancerous cells with alpha particles in an individual in need of such treatment comprising the step of:
administering a Pharmacologically effective dose of an $^{225}$Ac conjugate comprising a functionalized chelant having the structure

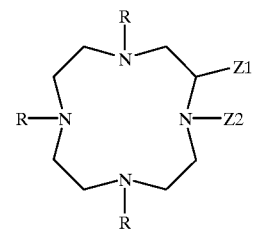

wherein R is independently CHQCO$_2$X;
Q is independently hydrogen; C$_{1-4}$-alkyl or (C$_{1-2}$-alkyl) phenyl;
X is independently hydrogen; benzyl or C$_{1-4}$-alky;
Z1 is (CH$_2$)$_n$Y wherein n is 1 to 10 and Y is an electrophilic or nucleophilic moiety and Z2 is R; or, in the alternative,
Z1 is hydrogen and Z2 is a peptide linker composed of 1–10 amino acids; and
an antibody or fragment thereof, a growth factor or a cytokine specifically targetable to said cancerous cells covalently attached to said Y or to said peptide linker; or a pharmaceutically acceptable salt thereof, complexed with $^{225}$Ac; and
targeting said antibody or antibody fragment, growth factor or a cytokine to said cancerous cells wherein said $^{225}$Ac or alpha particle-emitting daughters thereof emit said alpha particles Into said cancerous cells, said alpha particles causing a cytotoxic effect on said cancerous cells, thereby effecting treatment of said individual.

4. The method of claim 3, wherein said electrophilic or nucleophilic moiety is selected from the group consisting of p-isothiocyanatobenzene maleimides, vinylpyridine and NHS esters.

5. The method of claim 3, wherein In said chelant R and Z2 are CH$_2$CO$_2$H and Z1 is (CH$_2$)$_n$Y.

6. The method of claim 5, wherein said chelant is 2-(p-isothiocyanatobenzyl)-1,4,7,10-tetraazocyclododecane 1,4,7,10-tetraacetic acid.

7. The method of claim 3, wherein said antibody is IgG.

8. The method of claim 3, wherein said antibody is a monoclonal antibody.

9. The method of claim 8, wherein said monoclonal antibody is an internalizing antibody.

10. The method of claim 9, wherein said internalizing monoclonal antibody is selected from the group consisting of HuM195, J591, B4 and 3F8.

11. The method of claim 3, wherein said cancerous cells comprise a disseminated cancer or a solid tumor cancer.

12. The method of claim 11, wherein said cancers are selected from the group consisting of prostate cancer, lymphoma, leukemia, neuroblastomas, breast cancer and ovarian cancer.

13. The method of claim 3, wherein said $^{225}$Ac conjugate is administered as a pharmaceutical composition comprising said $^{225}$Ac conjugate and a pharmaceutical carrier.

14. A method of treating cancerous cells with alpha particles in an individual in need of such treatment comprising:
   administering a pharmacologically effective dose of an $^{225}$Ac conjugate comprising a functionalized chelant having the structure

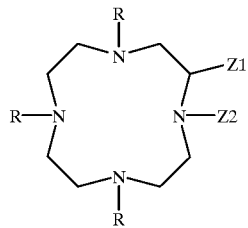

wherein R and Z2 are $CH_2CO_2H$; and
   Z1 is $(CH_2)_nY$ wherein n is 1 to 10 and Y is an electrophilic or nucleophilic moiety; said Y covalently attached to a monoclonal antibody; or a pharmaceutically acceptable salt thereof; complexed with $^{225}$Ac;
   binding said monoclonal antibody to said cancerous cells;
   internalizing said $^{225}$Ac within said cancerous cells, and emitting said alpha particles from said $^{225}$Ac or its daughters, said alpha particles remaining within said cancerous cells, wherein said alpha particles cause a cytoxic effect on said cancerous cells thereby effecting treatment of said individual.

15. The method of claim 14, wherein said electrophilic or nucleophilic moiety is selected from the group consisting of p-isothiocyanatobenzene, maleimides, vinylpyridine and NHS esters.

16. The method of claim 14, wherein said chelant is 2-(p-isothiocyanatobenzyl)-1,4,7,10-tetraazocyclododecane-1,4,7,10-tetraacetic acid.

17. The method of claim 16, wherein said monoclonal antibody is selected from the group consisting of HuM195, J591, B4 and 3F8.

18. The method of claim 14, wherein said cancerous cells comprise a disseminated cancer or a solid turn or Cancer.

19. The method of claim 18, wherein said cancers are selected from the group consisting of prostate cancer, lymphoma, leukemia, neuroblastomas breast cancer and ovarian cancer.

20. The method of claim 14, wherein said $^{225}$Ac conjugate is administered as a pharmaceutical composition comprising said $^{225}$Ac conjugate and a pharmaceutical carrier.

* * * * *